United States Patent [19]
Kondo et al.

[11] Patent Number: 5,488,038
[45] Date of Patent: Jan. 30, 1996

[54] DIBEKACIN DERIVATIVES AND ARBEKACIN DERIVATIVES ACTIVE AGAINST RESISTANT BACTERIA

[75] Inventors: Shinichi Kondo, Yohohama; Seiji Shibahara, Machida; Takayuki Usui, Kawasaki; Toshiaki Kudo, Yokohama; Shuichi Gomi, Tokyo; Atsushi Tamura, Yokohama; Yoko Ikeda, Tokyo; Daishiro Ikeda, Tokyo; Tomio Takeuchi, Tokyo, all of Japan

[73] Assignee: Zaidan Hojin Biseibutsu Kagaku Kenkyu Kai, Tokyo, Japan

[21] Appl. No.: 154,002

[22] Filed: Nov. 18, 1993

[30] Foreign Application Priority Data

Nov. 27, 1992 [JP] Japan .................................. 5-341314
Sep. 9, 1993 [JP] Japan .................................. 5-247327

[51] Int. Cl.$^6$ ........................... A61K 31/70; C07H 15/22
[52] U.S. Cl. ........................... 514/41; 536/13.7; 536/13.8
[58] Field of Search ........................... 536/13.7, 13.8; 514/41

[56] References Cited

U.S. PATENT DOCUMENTS

| | | | |
|---|---|---|---|
| 4,107,424 | 8/1978 | Umezawa et al. | 336/13.7 |
| 4,156,078 | 5/1979 | Umezawa et al. | 536/13.7 |
| 4,187,372 | 2/1980 | Carney et al. | 536/13.7 |
| 4,873,225 | 10/1989 | Umezawa et al. | 536/13.7 |

*Primary Examiner*—Elli Peselev
*Attorney, Agent, or Firm*—Larson and Taylor

[57] ABSTRACT

As new dibekacin derivatives and new arbekacin derivatives are now provided 2"-amino-2"-deoxydibekacin, 2"-amino-5,2"-dideoxydibekacin, 2"-amino-2"-deoxyarbekacin, 2"-amino-5,2"-dideoxyarbekacin, 2"-amino-5,2"-dideoxy-5-epi-fluoroarbekacin and 2"-amino-5,2"-dideoxy-5-epi-aminoarbekacin which all exhibit high antibacterial activity against a wide variety of gram-positive and gram-negative bacteria, including resistant bacteria such as methicillin-resistant *Staphylococcus aureus* and which are of low toxicity to mammals and are useful as antibacterial agent for treatment of bacterial infections.

6 Claims, No Drawings

DIBEKACIN DERIVATIVES AND ARBEKACIN DERIVATIVES ACTIVE AGAINST RESISTANT BACTERIA

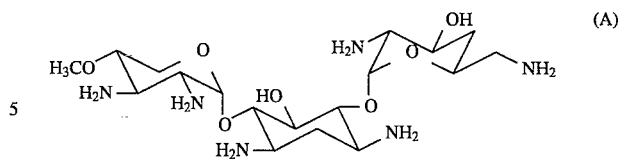

FIELD OF THE INVENTION

This invention relates to new compounds, 2"-amino-2"-deoxydibekacin and 2"-amino-2"-deoxyarbekacin as well as their 5-deoxy derivatives which are active against a wide variety of gram-positive and gram-negative bacteria and also against resistant bacteria, including resistant strains of Staphylococcus aureus. This invention also relates to another new compounds, 2"-amino-5,2"-dideoxy-5-epi-fluoroarbekacin and 2"-amino-5,2"-dideoxy-5-epi-aminoarbekacin which are active against a wide variety of gram-positive and gram-negative bacteria and also against resistant bacteria, including resistant strains of Staphylococcus aureus. These new compounds are of low toxicity and are useful as chemotherapeutic agent for therapeutic treatment of bacterial infections. This invention further relates to processes for the preparation of the above-mentioned new compounds. This invention further includes an antibacterial or a pharmaceutical composition comprising one of these new compounds as active ingredient.

BACKGROUND OF THE INVENTION

In 1967, the present inventors, and their associates investigated the resistance mechanism of resistant bacteria against some aminoglycosidic antibiotics such as streptomycin and kanamycins which were used widely as chemotherapeutic agents towards 1967, and elucidated for the first time the resistance mechanism such that these antibiotics can be inactivated by the action of various modifying enzymes as produced by the resistant bacteria. Then, further investigations were conducted, where a variety of kanamycin derivatives which cannot be inactivated by these modifying enzymes were synthetically prepared. Some sucesses were then obtained in proving the resistance mechanism of resistant bacteria against such kanamycin derivatives and also providing such various kanamycin derivatives which are actually useful as chemotherapeutic agents for bacterial infections [see, H. Umezawa and S. Kondo: "Aminoglycoside Antibiotics" edited by H. Umezawa and I. R. Hooper, Springer-Verlag, Berlin, Heidelberg, New York, page 267 (1982); and S. Kondo: "Biochemistry of Drug Resistance Mechanism", edited by S. Mitsuhashi, published by Gakkai Publishing Center, page 27 (1981)].

Amongst these kanamycin derivatives, 3',4'-dideoxykanamycin B, i.e. dibekacin [H. Umezawa et al., "J. Antibiotics", 24, 485 (1971)] has been used widely as chemotherapeutic agent active against drug-resistant bacteria since 1975. On the other hand, (S)-1-N-(4-amino-2-hydroxybutyryl)dibekacin, i.e. arbekacin [S. Kondo et al., "J. Antibiotics", 26, 412, (1973)] has been used as a specific medicine for treating infections with methicillin-resistant Staphylococcus aureus (MRSA) since the end of 1990.

In the meanwhile, there was known only one compound named seldomycin factor-5 as such an aminoglycosidic antibiotic which contains deoxystreptamine whose 2"- and 3"-positions each bear an amino group and which has the following formula (A):

Seldomycin factor-5 is produced by Streptomyces hofunensis [J. B. McAlpine et al., "J. Antibiotics", 30, 39 (1977)], but this antibiotic compound is clearly different in its chemical structure and antibacterial activity from the new 2"-amino-2"-deoxy derivatives of dibekacin and arbekacin now provided according to this invention.

In recent years, methicillin-resistant Staphylococcus aureus (MRSA) has brought about such a serious trouble that this bacterial strain rapidly propagated through hospital infections, leading to very serious infectious diseases. Thus the development of effectively usable therapeutic agents therefor is being earnestly wanted. Arbekacin has now been used for more than one year, but there has appeared yet no arbekacin-resistant strain of MRSA (which will show a minimum growth inhibitory concentration of arbekacin of not less than 25 µg/ml), in clinics. Since, however, there has been found the presence of such a strain of MRSA which exhibits a moderate+resistance to arbekacin (with showing a minimum growth inhibitory concentration of arbekacin between 6.25–12.5 µg/ml), we, the present inventors, have investigated detaildly the resistance mechanism of the MRSA strain having the moderate resistance to arbekacin. As a result, we have affirmed that the resistance mechanism of MRSA to arbekacin is due primarily to an enzymatic inactivation of arbekacin by phosphorylation of the 2"-OH group of arbekacin.

Based on these findings, we have further proceeded our study with the intention of synthesizing such novel derivatives of dibekacin or arbekacin which are not or little susceptible of the enzymatic phosphorylation. Thus, an object of this invention is to provide new dibekacin or arbekacin derivatives which are obtainable from dibekacin through chemical syntheses, which have broad and effective antibacterial activities not only against MRSA, but also against gram-positive and gram-negative bacteria, and which are of low toxicity.

DETAILED DESCRIPTION OF THE INVENTION

We have now succeeded, as a result of these investigations, in synthesizing novel arbekacin derivatives which have such structure that the 2"-hydroxyl group of arbekacin susceptible of being phosphorylated has been converted into an amino group, namely, 2"-amino-2"-deoxyarbekacin and 2"-amino-5,2"-dideoxyarbekacin represented by the undermentioned general formula (I). And, we have also succeeded in synthesizing novel dibekacin derivatives which have such structure that the 2"-hydroxyl group of dibekacin has been converted into an amino group, namely, 2"-amino-2"-deoxydibekacin and 2"-amino-5,2"-dideoxydibekacin represented by the undermentioned general formula (II). We have further found that the above-mentioned novel two arbekacin derivatives and novel two dibekacin derivatives thus synthesized not only strongly inhibit the growth of methicillin-resistant Staphylococcus aureus (MRSA), but also exhibit broad and effective antibacterial activities against gram-positive and gram-negative bacteria, with having low toxicity to mammals.

According to a first aspect of this invention, therefore, there are provided 2"-amino-2"-deoxyarbekacin or 5-deoxy derivative thereof represented by the following general formula (i)

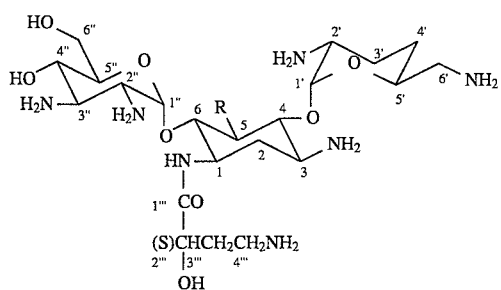

wherein R means a hydroxyl group or a hydrogen atom, and an acid addition salt thereof.

The compound of general formula (I) where R means a hydroxyl group is 2"-amino-2"-deoxyarbekacin represented by the following formula (Ia)

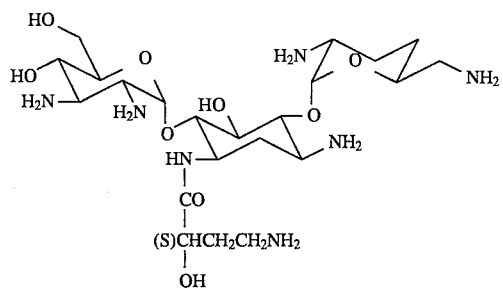

The compound of general formula (I) where R means a hydrogen atom is 2"-amino-5,2"-dideoxyarbekacin represented by the following formula (Ib)

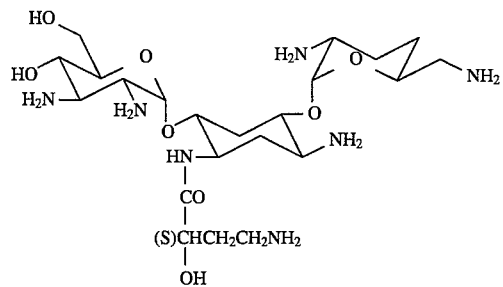

Further, according to a second aspect of this invention, there are provided 2"-amino-2"-deoxydibekacin or 5-deoxy derivative thereof represented by the following general formula (II)

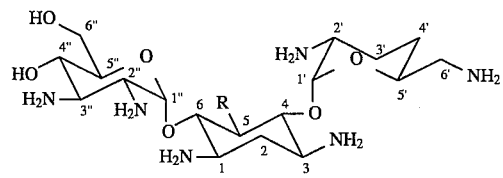

wherein R means a hydroxyl group or a hydrogen atom, and an acid addition salt thereof.

The compound of general formula (II) where R means a hydroxyl group is 2"-amino-2"-deoxydibekacin represented by the following formula (IIa)

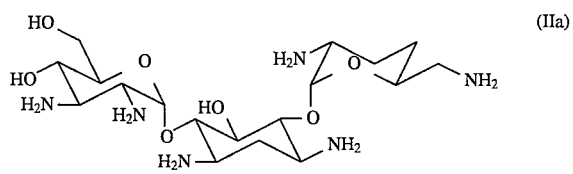

The compound of general formula (II) where R means a hydrogen atom is 2"-amino-5,2"-dideoxydibekacin represented by the following formula (IIb)

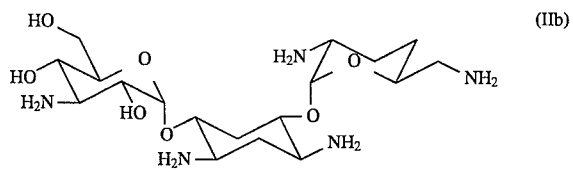

Physico-chemical properties of the new 2"-amino-2"-deoxy derivatives of arbekacin and dibekacin and their 5-deoxy derivatives having general formula (I) and (II), respectively, as obtained according to this invention are described below:

[1] 2"-Amino-2"-deoxyarbekacin [Compound Ia]
  (1) Color and form: colorless powder
  (2) Molecular formula: $C_{22}H_{45}N_7O_9$
  (3) Mass spectrum(SI-MS): m/z 552(M+H)$^+$
  (4) Melting point: 155°–160° C. (decomposed)
  (5) Optical rotation: $[\alpha]_D^{20}+86°$ (c 0.53 $H_2O$)
  (6) UV and visible ray-absorption spectra: no specific absorption
  (7) Infrared absorption spectrum: 3380, 2930, 1650, 1580, 1470, 1380, 1320, 1100, 1020 cm$^{-1}$
  (8) $^1$H-NMR spectrum($D_2O$, pD 2): as shown in TABLE 1 hereinafter
  (9) $^{13}$C-NMR spectrum($D_2O$, pD 2): as shown in TABLE 2 hereinafter
  (10) Solubility: easily soluble in water
  (11) Distinction between basic, acidic and neutral substances in nature: basic substance

[2] 2"-Amino-5,2"-dideoxyarbekacin [Compound Ib]
  (1) Color and form: colorless powder
  (2) Molecular formula; $C_{22}H_{45}N_7O_8$
  (3) Mass spectrum(FD-MS): m/z 536(M+H)$^+$
  (4) Melting point: 196°–198° C. (decomposed)
  (5) Optical rotation: $[\alpha]_D^{20}+92°$ (c 0.74, $H_2O$)
  (6) UV and visible ray-absorption spectra: no specific absorption
  (7) Infrared absorption spectrum: 3400, 2940, 1650, 1580, 1460, 1390, 1340, 1040 cm$^{-1}$
  (8) $^1$H-NMR spectrum($D_2O$, pD 2): as shown in TABLE 1 hereinafter
  (9) $^{13}$C-NMR spectrum($D_2O$, pD 2): as shown in TABLE 2 hereinafter
  (10) Solubility: easily soluble in water
  (11) Distinction between basic, acidic and neutral substances in nature: basic substance

[3] 2"-Amino-2"-deoxydibekacin [Compound IIa]
  (1) Color and form: colorless powder
  (2) Molecular formula; $C_{18}H_{38}N_6O_7$
  (3) Mass spectrum(SI-MS): m/z 451(M+H)$^+$
  (4) Melting point: 129°–133° C. (decomposed)
  (5) Optical rotation: $[\alpha]_D^{20}+122°$ (c 0.39, $H_2O$)

(6) UV and visible ray-absorption spectra: no specific absorption (7) Infrared absorption spectrum: 3350, 2930, 1580, 1480, 1380, 1340, 1120, 1020 cm$^{-1}$ (8) $^1$H-NMR spectrum(D$_2$O, pD 2): as shown in TABLE 1 hereinafter (9) $^{13}$C-NMR spectrum(D$_2$O, pD 2): as shown in TABLE 2 hereinafter

(10) Solubility: easily soluble in water

(11) Distinction between basic, acidic and neutral substances in nature: basic substance

[4] 2"-Amino-5,2"-dideoxydibekacin [Compound IIb]

(1) Color and form: colorless powder (2) Molecular formula: C$_{18}$H$_{38}$N$_6$O$_6$ (3) Mass spectrum(SI-MS): m/z 435(M+H)$^+$ (4) Melting point: 129°–131° C. (decomposed)

(5) Optical rotation: $[\alpha]_D^{20}$+166° (c 0.51, H$_2$O)

(6) UV and visible ray-absorption spectra: no specific absorption (7) Infrared absorption spectrum: 3350, 2940, 1590, 1460, 1380, 1340, 1100, 1020 cm$^{-1}$ (8) $^1$H-NMR spectrum(D$_2$O, pD 2): as shown in TABLE 1 hereinafter (9) $^{13}$C-NMR spectrum(D$_2$O, pd 2): as shown in TABLE 2 hereinafter

(10) Solubility: easily soluble in water

(11) Distinction between basic, acidic and neutral substances in nature: basic substance

TABLE 1

Chemical Shift in deutero-water (pD 2) (ppm*)

| Proton | Compound Ia | Compound Ib | Compound IIa | Compound IIb |
|---|---|---|---|---|
| 1-H | 4.20 ddd | 4.08 m | 3.79 m | 3.70 m |
| 2-H$_{ax}$ | 1.98 ddd | 1.79 ddd | 2.18 ddd | 1.96 ddd |
| 2-H$_{eq}$ | 2.33 ddd | 2.34 ddd | 2.58 ddd | 2.58 ddd |
| 3-H | 3.58 ddd | 3.52 ddd | 3.64 ddd | 3.60 ddd |
| 4-H | 4.06 dd | 4.06 m | 4.19 m | 4.11 ddd |
| 5-H$_{ax}$ | 3.95 dd | 1.72 ddd | 4.18 m | 1.76 ddd |
| 5-H$_{eq}$ | | 3.00 dd | | 3.21 ddd |
| 6-H | 4.13 dd | 4.09 m | 4.15 dd | 4.17 ddd |
| 1'-H | 5.82 d | 5.39 d | 5.76 d | 5.40 d |
| 2'-H | 3.62 ddd | 3.57 ddd | 3.59 ddd | 3.57 ddd |
| 3'-H$_2$ | 2.08 m | 2.04 m | 2.04 m | 2.05 m |
| 4'-H$_{ax}$ | 1.67 dddd | 1.59 m | 1.64 dddd | 1.62 m |
| 4'-H$_{eq}$ | 1.99 m | 1.90 m | 1.95 m | 1.92 m |
| 5'-H | 4.24 m | 4.06 m | 4.22 m | 4.08 m |
| 6'-H$_2$ | 3.17 dd | 3.08 dd | 3.14 dd | 3.10 dd |
|  | 3.32 dd | 3.26 dd | 3.28 dd | 3.28 dd |
| 1"-H | 5.52 d | 5.45 d | 5.72 d | 5.55 d |
| 2"-H | 3.86 m | 3.84 dd | 3.98 dd | 3.80 dd |
| 3"-H | 3.87 dd | 3.74 dd | 3.87 dd | 3.72 m |
| 4"-H | 3.86 m | 3.69 dd | 3.80 dd | 3.71 m |
| 5"-H | 4.13 m | 3.95 m | 4.18 m | 3.98 m |
| 6"-H$_2$ | 3.88 dd | 3.75 dd | 3.79 dd | 3.76 dd |
|  | 3.93 dd | 3.96 m | 3.98 m | 3.96 dd |
| 2'''-H | 4.37 dd | 4.33 dd | | |
| 3'''-H$_2$ | 2.01 m | 1.94 dddd | | |
|  | 2.22 ddt | 2.19 dddd | | |
| 4'''-H$_2$ | 3.22 t | 3.17 m | | |

*Sodium trimethylsilylpropionate was deemed as giving 0 ppm.

TABLE 2

Chemical shift in deutero-water (pD 2) (ppm*)

| Carbon | Compound Ia | Compound Ib | Compound IIa | Compound IIb |
|---|---|---|---|---|
| 1 | 50.1 d | 51.6 d | 49.7 d | 51.6 d |
| 2 | 31.1 t | 31.0 t | 29.1 t | 29.2 t |
| 3 | 49.4 d | 52.0 d | 48.9 d | 51.5 d |
| 4 | 78.2 d | 71.2 d | 78.3 d | 70.9 d |
| 5 | 75.0 d | 33.9 t | 74.6 d | 33.0 t |
| 6 | 78.3 d | 77.9 d | 81.8 d | 78.3 d |
| 1' | 96.0 d | 90.7 d | 96.3 d | 90.8 d |
| 2' | 49.6 d | 48.9 d | 49.6 d | 48.8 d |
| 3' | 21.3 t | 21.7 t | 21.3 t | 21.6 t |
| 4' | 26.2 t | 26.3 t | 26.1 t | 26.2 t |
| 5' | 66.8 d | 66.4 d | 67.0 d | 66.5 d |
| 6' | 43.4 t | 43.4 t | 43.3 t | 43.3 t |
| 1" | 93.8 d | 96.3 d | 94.6 d | 96.9 d |
| 2" | 51.7 d | 51.6 d | 51.7 d | 51.8 d |
| 3" | 53.0 d | 52.9 d | 52.8 d | 53.1 d |
| 4" | 65.8 d | 66.4 d | 66.3 d | 66.6 d |
| 5" | 72.8 d | 73.1 d | 73.8 d | 73.1 d |
| 6" | 60.4 t | 61.2 t | 60.8 t | 61.2 t |
| 1''' | 176.4 s | 176.3 s | | |
| 2''' | 70.3 d | 70.2 d | | |
| 3''' | 31.5 t | 31.7 t | | |
| 4''' | 37.6 t | 37.6 t | | |

*Dioxane (67.4 ppm) was used as internal standard.

Acid addition salts of 2"-amino-2"-deoxyarbekacin and 2"-amino-5,2"-dideoxyarbekacin having general formula (I) and of 2"-amino-2"-deoxydibekacin and 2"-amino-5,2"-dideoxydibekacin having general formula (II) according to this invention include such those with pharmaceutically acceptable inorganic acids such as hydrochloric acid, sulfuric acid, phosphoric acid, nitric acid, etc. and such those with pharmaceutically acceptable organic acids such as malic acid, citric acid, ascorbic acid, methanesulfonic acid, etc.

Biological properties of the new 2"-amino-2"-deoxy derivatives of dibekacin and arbekacin, and their 5-deoxy derivatives obtained according to this invention are described below:

(1) Antibacterial activities

Minimum growth inhibitory concentrations (MIC) of each of 2"-amino-2"-deoxyarbekacin (Compound Ia), 2"-amino-5,2"-dideoxyarbekacin (Compound Ib), 2"-amino-2"-deoxydibekacin (Compound IIa) and 2"-amino-5,2"-dideoxy-dibekacin (Compound IIb) against various bacteria (20 strains) and against clinically isolated strains of MRSA (50 strains) were determined by standard serial dilution method on Müller-Hinton's agar medium (as estimated after cultivating at 27° C. for 18 hours), and the test results obtained are shown in TABLE 3 and TABLE 4, respectively.

TABLE 3

| Test organisms | MIC. (µg/ml) | | | |
|---|---|---|---|---|
|  | Compound Ia | Compound Ib | Compound IIa | Compound IIb |
| Staphylococcus aureus FDA209P | 0.39 | ≦0.20 | 0.78 | 0.39 |
| S. aureus Smith | ≦0.20 | ≦0.20 | 0.39 | ≦0.20 |
| S. epidermidis 109 | 0.78 | 0.39 | 1.56 | 0.78 |
| Bacillus subtilis PCI219 | 0.20 | ≦0.20 | ≦0.20 | ≦0.20 |
| B. cereus ATCC10702 | 3.13 | 0.78 | 3.13 | 1.56 |
| Escherichia coli NIHJ | 0.78 | 0.39 | 0.78 | 1.56 |
| E. coli K-12 ML1629 | 3.13 | 1.56 | 3.13 | 6.25 |

TABLE 3-continued

| | MIC. (μg/ml) | | | |
|---|---|---|---|---|
| Test organisms | Compound Ia | Compound Ib | Compound IIa | Compound IIb |
| E. coli K-12 ML1410 | 1.56 | 1.56 | 1.56 | 3.13 |
| E. coli K-12 LA290 R55 | 0.78 | 0.78 | 1.56 | 3.13 |
| E. coli JR66/W677 | 3.13 | 3.13 | 3.13 | 6.25 |
| Klebsiella pneumoniae PCI602 | 1.56 | 0.78 | 3.13 | 3.13 |
| Shigella dysenteriae JSI1910 | 3.13 | 1.56 | 3.13 | 6.25 |
| Salmonella typhi T-63 | 0.78 | 0.78 | 1.56 | 3.13 |
| Proteus vulgaris OX19 | 1.56 | 0.78 | 1.56 | 1.56 |
| Providencia rettgeri GN311 | 1.56 | 0.78 | 1.56 | 1.56 |
| Serratia marcescens | 3.13 | 6.25 | 12.5 | 25 |
| Pseudomonas aeruginosa A3 | 1.56 | 0.39 | 1.56 | 0.78 |
| P. aeruginosa H9 | 6.25 | 3.13 | 6.25 | 12.5 |
| P. aeruginosa TI-13 | 3.13 | 1.56 | 3.13 | 3.13 |
| P. aeruginosa PST1 | 12.5 | 6.25 | 50 | 100 |

TABLE 4

| Test compound | Antibacterial MIC spectra (μg/ml) against 50 clinically isolated strains of MRSA | $MIC_{50}$ | $MIC_{90}$ |
|---|---|---|---|
| Compound Ia | 0.20–3.13 | 0.78 | 1.56 |
| Compound Ib | 0.20–3.13 | 0.78 | 1.56 |
| Compound IIa | ≦0.20–50 | 6.25 | 25 |
| Compound IIb | 0.78–25 | 3.13 | 25 |
| DKB (comparative) | ≦0.20–>100 | 50 | >100 |
| ABK (comparative) | ≦0.20–6.25 | 0.39 | 6.25 |

Note:
$MIC_{50}$ or $MIC_{90}$ represents the concentration of tested active compound at which 50% or 90% of the total numbers of the bacterial strains tested were inhibited from their growth. DKB denotes dibekacin, and ABK denotes arbekacin.

(2) Acute toxicity

50% Lethal dosages ($LD_{50}$, observations for two weeks) of the new compounds of this invention as estimated upon single intravenous administration to mice (ICR-strain, 4 weeks old, female) are as follows:

| | $LD_{50}$ |
|---|---|
| 2"-Amino-2"-deoxyarbekacin (Compound Ia) | >100 mg/kg |
| 2"-Amino-5,2"-dideoxyarbekacin (Compound Ib) | 50–100 mg/kg |
| 2"-Amino-2"-deoxydibekacin (Compound IIa) | >100 mg/kg |
| 2"-Amino-5,2"-dideoxydibekacin (Compound IIb) | 50–100 mg/kg |

Based on the above elucidation of the biological properties of the new compounds of general formula (I) and (II) according to this invention, it has been proved that these new compounds not only inhibit strongly the growth of methicillin-resistant *Staphylococcus aureus,* but also have broad and highly effective antibacterial activities against gram-positive and gram-negative bacteria, including *Pseudomonas aeruginosa* and are of low toxicity to mammals.

The compounds of general formula (I) and the compounds of general formula (II) or acid addition salts thereof according to this invention may be formulated into various antibacterial compositions containing the said compound(s) as active ingredient by blending the same with pharmaceutically acceptable liquid or solid carrier(s) which may be used conventionally. Anti-bacterial compositions containing the compounds of general formula (I) or (II) or their acid addition salts of this invention may be used primarily in various formulations for administration, including injections such as intra-venous injections, oral compositions such as capsules, tablets, powder and granules, and others such as ointment, intrarectal agent, suppositories of oil-fat type, water-soluble suppositories, and the like. These various formulations may be prepared in any conventional manner using conventional excipients, fillers, binders, wetting agents, disintegrators, surfactants, lubricants, dispersants, buffers, preservatives, dissolution aids, antiseptics, flavorings, indolent agents, and the like.

Generally speaking, 2"-amino-2"-deoxyarbekacin and 2"-amino-5,2"-dideoxyarbekacin as represented by general formula (I) according to the first aspect of this invention, as well as 2"-amino-2"-deoxydibekacin and 2"-amino-5,2"-dideoxydibekacin as represented by general formula (II) according to the second aspect of this invention may be prepared by converting the 2"-hydroxyl group of dibekacin into amino group, and if necessary, acylating the 1-amino group of the resulting aminated product with (s)-4-amino-2-hydroxybutyric acid, followed by replacing the 5-hydroxyl group by a hydrogen atom.

As a process for producing 2"-amino-2"-deoxy-arbekacin of formula (Ia) according to the first aspect of this invention, there is provided, in a third aspect of this invention, a process for the preparation of 2"-amino-2"-deoxyarbekacin of the following formula (Ia)

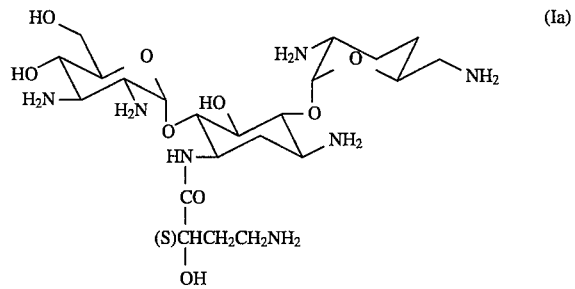

(Ia)

which comprises the steps of:
protecting each of the 1- and 3"-amino groups of 3,2',6'-N-tris(alkoxycarbonyl)-dibekacin represented by general formula (III)

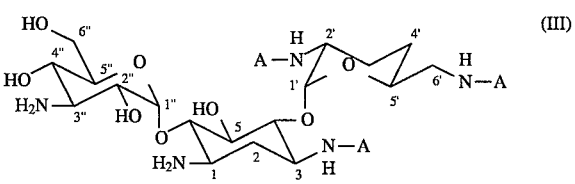

(III)

wherein A means an alkoxycarbonyl group serving as an amino-protecting group removable by hydrolysis, with an aralkyloxycarbonyl group which is an amino-protecting group removable by hydrogenolysis, to form a 1,3"-N-bis(aralkyl-oxycarbonyl)-3,2',6'-N-tris(alkoxycarbonyl)-dibekacin represented by general formula (IV)

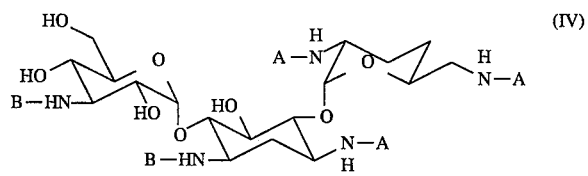

(IV)

wherein A has the meaning as defined above and B means an aralkyloxycarbonyl group;
protecting both of the two hydroxyl groups at the 4"- and 6"-positions of the compound of general formula (IV) with an aralkylidene or alkylidene group as a hydroxyl-protecting group, to form a 4",6"-O-aralkylidene or alkylidene-1,3"-N-bis (aralkyloxycarbonyl)-3,2',6'-N-tris-(alkoxycarbonyl)-dibekacin represented by the following formula (V)

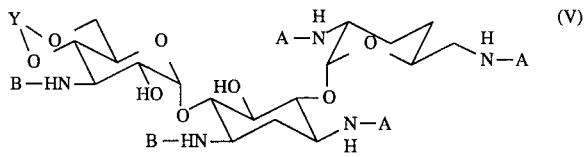

wherein A and B have the meanings as defined above and Y means an aralkylidene or alkylidene group;

oxidizing the 2"-hydroxyl group of the compound of formula (V) with an oxidizing agent to form a 4",6"-O-aralkylidene or alkylidene-1,3"-N-bis(aralkyloxycarbonyl)-3,2',6'-N-tris(alkoxycarbonyl)-2"-deoxy-2"-oxodibekacin represented by the following formula (VI)

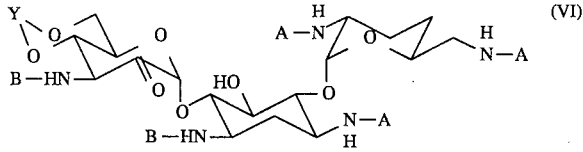

wherein A, B and Y have the meanings as defined above;

converting the 2"-oxo group of the compound of formula (VI) into 2"-amino group by reducing the same with a hydride in the presence of ammonium acetate, thereby to form a 2"-amino-4",6"-O-aralkylidene or alkylidene-1,3"-N-bis (aralkyloxycarbonyl)-3,2',6'-N-tris (alkoxycarbonyl)-2" -deoxydibekacin represented by the following formula (VII)

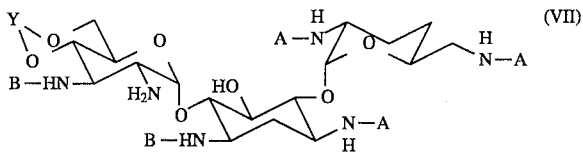

wherein A, B and Y have the meanings as defined above;

protecting the 2"-amino group of the compound of formula (VII) with an alkoxycarbonyl group (A) to form a 2"-amino-4",6"-O-aralkylidene or alkylidene-1,3" -N-bis-(aralkyloxycarbonyl)-3,2',6',2"-N-tetrakis(alkoxycarbonyl)-2"-deoxydibekacin represented by the following formula (VIII)

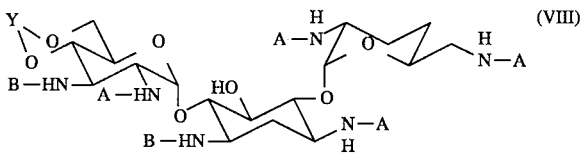

wherein A, B and Y have the meanings as defined above;

eliminating the aralkyloxycarbonyl groups (B) from the 1- and 3"-amino groups by hydrogenolysis to form a 2"-amino-4",6"-O-aralkylidene or alkylidene-3,2',6', 2" -N-tetrakis (alkoxycarbonyl)-2"-deoxydibekacin represented by the following formula (IX)

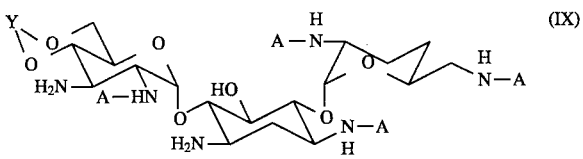

wherein A and Y have the meanings as defined above;

acylating the 1-amino group of the compound of formula (IX) with an active ester or acid halide of (S)-4 -(p-alkoxy-substituted-benzyloxycarbonyl- or alkoxycarbonylamino)- 2-hydroxybutyric acid represented by the following formula (X)

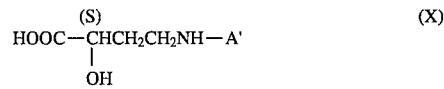

wherein A' means a p-alkoxy-substituted-benzyloxycarbonyl or alkoxycarbonyl group as an amino-protecting group removable by hydrolysis, to form a 1-N-[(S)-4 -(p-alkoxy-substituted-benzyloxycarbonyl- or alkoxycarbonyl-amino)-2 -hydroxybutyryl]-2"-amino-4",6"-O-aralkylidene or alkylidene-3,2',6', 2" -N-tetrakis (alkoxycarbonyl)-2"-deoxydibekacin represented by the following formula (XI)

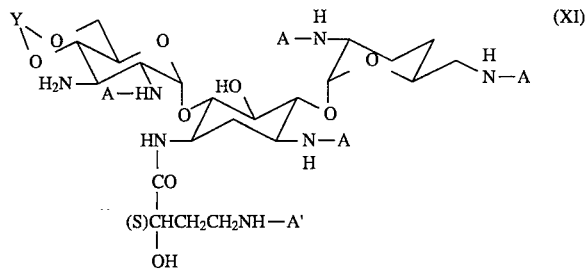

wherein A, Y and A' have the meanings as defined above; and hydrolyzing the compound of formula (XI) to remove therefrom the alkoxycarbonyl group (A), the p-alkoxy-substituted-benzyloxycarbonyl or alkoxycarbonyl group (A'), and the aralkylidene or alkylidene group (Y) and to produce the compound of formula (Ia)

3,2',6'-N-Tris(alkoxycarbonyl)-dibekacin of formula (III) to be used as the starting material in the process of the third aspect of this invention may be prepared by reacting dibekacin with an alkoxycarbonyl chloride or an active ester equivalant thereto in a suitable organic solvent such as tetrahydrofuran or dimethyl-sulfoxide in the presence of zinc cation in accordance with the process described in the specification of Japanese Patent Publication Sho-63-1319 or U.S. Pat. No. 4,297,485.

With respect to the process steps for the introduction of an alkoxycarbonyl group into each of the 1- and 3"-amino groups of the compound of formula (III), the introduction of an aralkyliden or alkylidene group into both of the 4"- and 6"-hydroxyl groups of the compound of formula (IV), the introduction of an alkoxycarbonyl group into the 2"-amino group of the compound of formula (VII), the deprotection of the protected 1- and 3"-amino groups of the compound of formula (VIII), and the deprotection of the 1-N-acylated compound of formula (XI), there may be used known techniques established and conventionally utilizable in the sugar chemistry for the purposes of the protection of amino group, protection of hydroxyl group, removal of amino-protecting group and removal of hydroxy-protecting group in a usual manner.

The oxidation of the 2"-hydroxyl group of the compound of formula (V) into oxo group may be carried out by Pfitzner-Moffatt's oxidation method, as illustrated hereinafter in relation to "Synthetic Process Chart A". Then, the conversion of the 2"-oxo group of the compound of formula (VI) into amino group may be effected by such known method for reduction with a hydride in the presence of ammonium acetate, as illustrated in "Synthetic Process Chart A".

Further, the step of acylating the 1-amino group of the compound of formula (IX) with an active ester or an acid halide of an N-protected-(S)-4-amino-2-hydroxybutyric acid of formula (X) may be carried out in accordance with the method for 1-N-acylation of kanamycins as described in the specifications of Japanese Patent Publication Sho-52-33629, U.S. Pat. No. 4,001,208 and U.S. Pat. No. 4,297,485.

Furthermore, as a process for producing 2"-amino-5,2"-dideoxyarbekacin of formula (Ib) according to the first aspect of this invention, there is provided, in a fourth aspect of this invention, a process for the preparation of 2"-amino-5,2"-dideoxyarbekacin of the following formula (Ib)

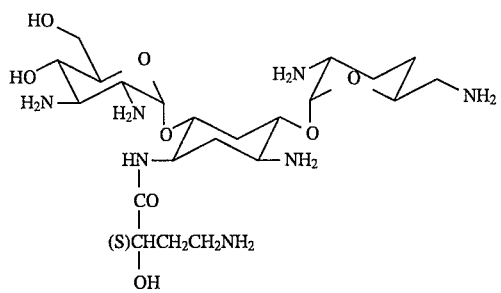

which comprises the steps of:

eliminating by a known deoxygenation method the 5-hydroxyl group of a 2"-amino-4",6"-O-aralkylidene or alkylidene-1,3"-N-bis (aralkyloxycarbonyi)-3,2',6'2" -N-tetrakis (alkoxycarbonyl)-2"-deoxydibekacin represented by general formula (VIII)

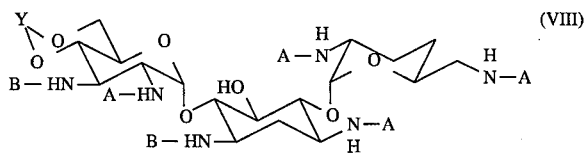

wherein A means an alkoxycarbonyl group, B means an aralkyl-oxycarbonyl group and Y means an aralkylidene or alkylidene group, to form a 2"-amino- 4",6"-O-aralkylidene or alkylidene- 1,3"-N-bis (aralkyloxycarbonyl)-3,2',6', 2"-N-tetrakis (alkoxycarbonyl)-5,2"-dideoxydibekacin represented by the following formula (XII)

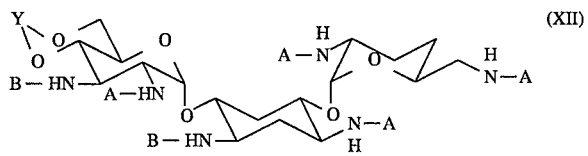

wherein A, B and Y have the meanings as defined above;

eliminating the aralkyloxycarbonyl groups (B) from the 1-and 3"-amino groups of the compound of formula (XII) to form a 2 "-amino-4",6"-O-aralkylidene or alkylidene-3,2', 6'2"-N-tetrakis (alkoxycarbonyl)-5,2"-dideoxydibekacin represented by the following formula (XIII)

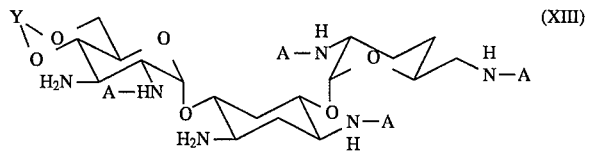

wherein A and Y have the meanings as defined above;

acylating the 1-amino group of the compound of formula (XIII) with an active ester or acid halide of (S)-4-(p-alkoxy-substituted-benzyloxycarbonyl- or alkoxycarbonyl-amino)-2-hydroxybutyric acid represented by the following formula (X):

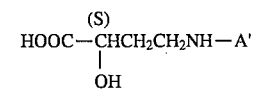

wherein A' means a p-alkoxy-substituted-benzyloxycarbonyl or alkoxycarbonyl group as an amino-protecting group removable by hydrolysis, to form a 1-N-[(S)-4-(p-alkoxy-substituted-benzyloxycarbonyl- or alkoxycarbonyl-amino)-2-hydroxybutyryl]- 2"-amino-4",6"-O-aralkylidene or alkylidene-3,2',6',2" -N-tetrakis(alkoxycarbonyl)-5,2"-dideoxydibekacin represented by the following formula (XIV)

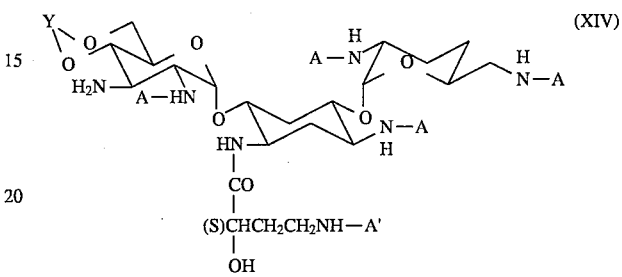

wherein A, Y and A' have the meanings as defined above; and hydrolyzing the compound of formula (XIV) to remove therefrom the alkoxycarbonyl group (A), the p-alkoxy-substituted-benzyloxycarbonyl or alkoxycarbonyl group (A'), and the aralkylidene or alkylidene group (Y) and to produce the compound of formula (Ib).

In the process of the fourth aspect of this invention, the deoxygenation method for effecting the elimination of the 5-hydroxyl group of the compound of formula (VIII) may conveniently be carried out by a two-stage process where the 5-hydroxyl group is first converted into dithiocarbonate group, followed by reducing the latter with a hydride as illustrated hereinafter in relation to "Synthetic Process Chart B". However, any other known deoxygenation method may be adopted, if desired.

The step for deprotection of the protected 1-and 3"-amino groups of the compound of formula (XII) and the step for deprotection of the 1-N-acylated product of formula (XIV) may be carried out in a usual manner similarly to the corresponding step in the process of the third aspect of this invention.

Further, the step of acylating the 1-amino group of the compound of formula (XIII) with the butyric acid derivative of formula (X) may be effected in a similar manner to that of the corresponding step in the process of the third aspect of this invention.

For production of 2"-amino-2"-deoxydibekacin of formula (IIa) according to the second aspect of this invention, there is provided, in a fifth aspect of this invention, a process for the preparation of 2"-amino-2"-deoxydibekacin of formula (IIa)

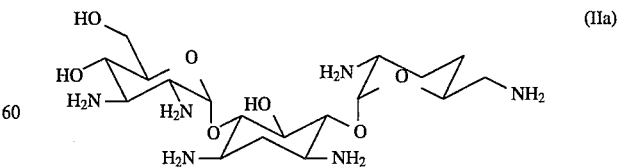

which comprises removing the aralkylidene or alkylidene group (Y) and alkoxycarbonyl group (A) of a 2"-amino-4"-, 6"-O-aralkylidene- or alkylidene-3,2',6',2" -N-tetrakis-(alkoxycarbonyl)-2"-deoxydibekacin represented by general formula (IX):

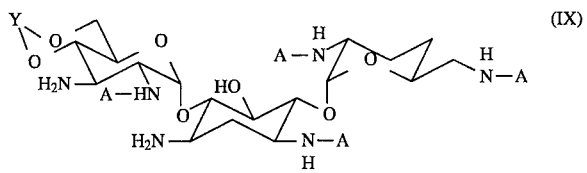

wherein A means an alkoxycarbonyl group and Y means an aralkylidene or alkylidene group, from the compound of formula (IX) to produce the compound of formula (IIa). Said 2"-amino-4",6"-O-aralkylidene- or alkylidene-3,2', 6', 2"-N-tetrakis (alkoxycarbonyl)-2"-deoxydibekacin of formula (IX) may have been synthesized via a series of compounds of general formulae (III), (IV), (V), (VI), (VII), and (VIII) mentioned hereinbefore.

Furthermore, for production of 2 "-amino-5,2" -dideoxy-dibekacin of formula (IIb) according to the second aspect of this invention, there is provided, in a sixth aspect of this invention, a process for the preparation of 2"-amino-5,2"-dideoxydibekacin of formula (IIb)

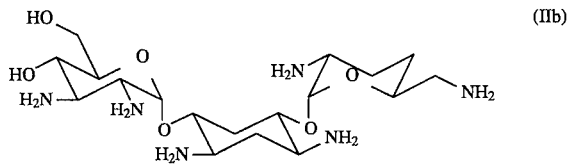

which comprises removing the aralkylidene or alkylidene group (Y) and alkoxycarbonyl group (A) of a 2"-amino-4", 6"-O-aralkylidene or alkylidene-3,2',6',2" -N-tetrakis-(alkoxycarbonyl)-5,2"-dideoxydibekacin represented by general formula (XIII):

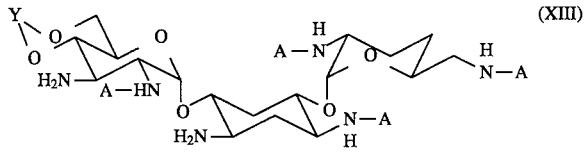

wherein A means an alkoxycarbonyl group and Y means an aralkylidene or alkylidene group, from the compound of formula (XIII) to produce the compound of formula (IIb). Said 2"-amino-4",6"-O-aralkylidene or alkylidene-3,2', 6',2"-N-tetrakis(alkoxycarbonyl)-5,2"-dideoxydibekacin of formula (XIII) may have been prepared via the compounds of general formulae (VIII) and (XII) as mentioned hereinbefore.

2"-Amino-2"-deoxydibekacin of formula (IIa) according to the second aspect of this invention is prepared as set forth in the fifth aspect of this invention hereinafter given. It is apparent that the process of the fifth aspect of this invention may also be applied to such cases when there is employed the compound of formula (IX) which has been prepared from the compounds of general formulae (IV), (V), (VI), (VII) and (VIII) where the amino-protecting groups A and B are equal to each other. Besides, the process of the sixth aspect of this invention for the production of 2"-amino-5, 2"-dideoxydibekacin of formula (IIb) may also be applied to such cases when there is employed the compound of general formula (XIII) which has been prepared from the compounds of general formulae (VIII) and (XII) where the amino-protecting groups A and B are equal to each other. As a known compound examples of the compound of general formula (IV) which is available as the starting material in the above cases and in which the amino-protecting groups A and B are the same, there may be employed 1,3,2',6',3" -N-pentakis(t-butyoxycarbonyl)dibekacin [see T. Miyasaka et al., "J. Antibiotics", 33, 527, (1980)].

Now, in respect of the process of the third aspect of this invention, there is given below "Synthetic Process Chart A" which briefly shows a preferred embodiment for carrying out the respective steps of the process of the third aspect of this invention, where 2"-amino-2" -deoxyarbekacin of formula (Ia) is synthesized starting from 3,2',6'-N-tris (t-butoxycarbonyl) dibekacin (Compound IIIa) which is a preferred example of compounds of general formula (III). In "Synthetic Process Chart A", Boc represents t-butoxycarbonyl group, Z represents benzyloxycarbonyl group, Ph denotes phenyl group, and PMZ denotes p-methoxybenzyloxycarbonyl group (the same applies to the other Charts given hereinafter).

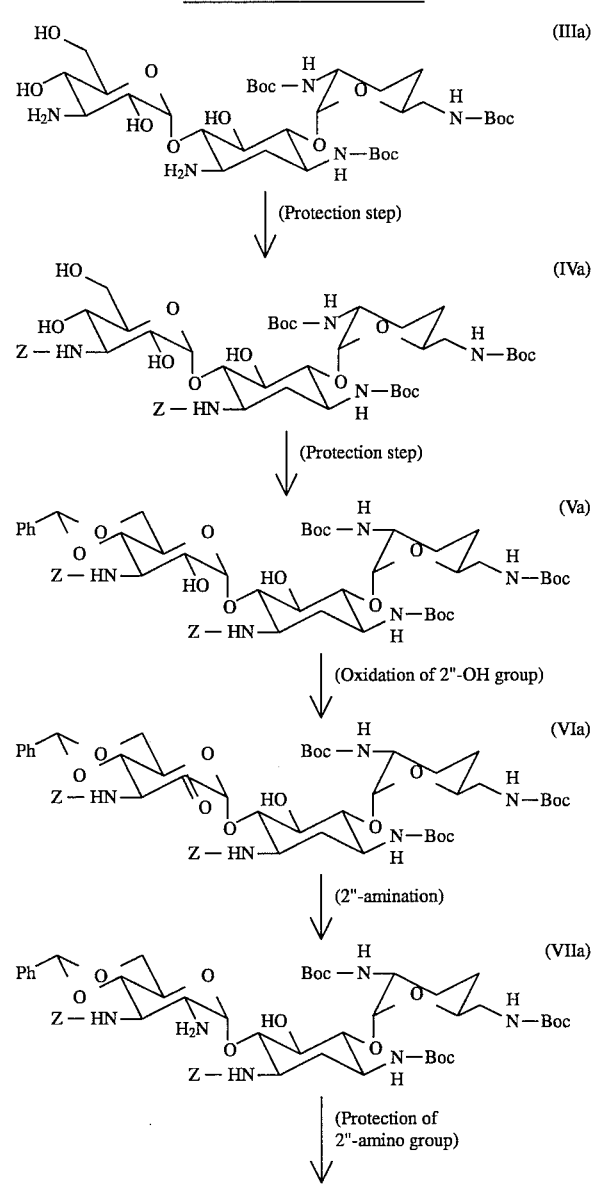

-continued
Synthetic Process Chart A

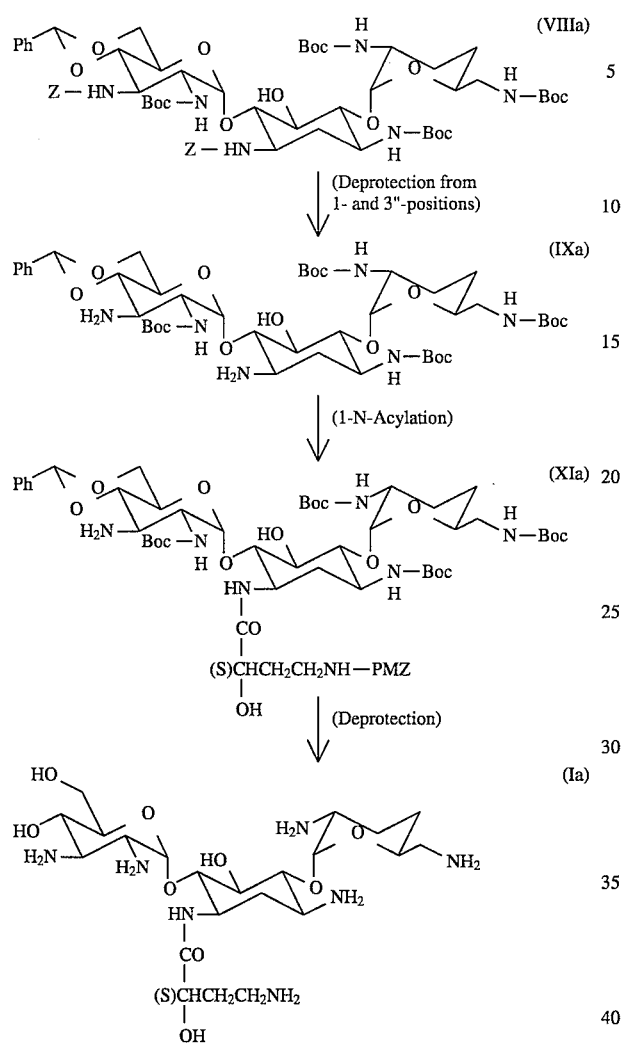

"Synthetic Process Chart B" given below briefly shows an embodiment for carrying out the respective steps of the process of the fourth aspect of this invention, where 2"-amino-5,2"-dideoxyarbekacin of formula (Ib) is synthesized using the compound of formula (VIIIa) which is obtained as an intermediate in "Synthetic Process Chart A" above which shows a preferred embodiment of the process of the third aspect of this invention.

Synthetic Process Chart B

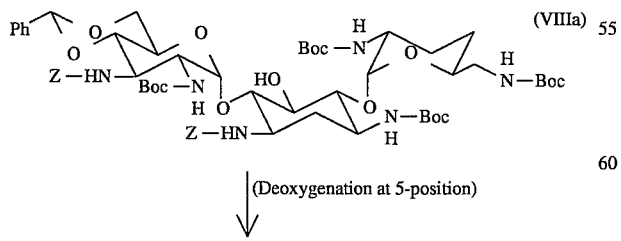

-continued
Synthetic Process Chart B

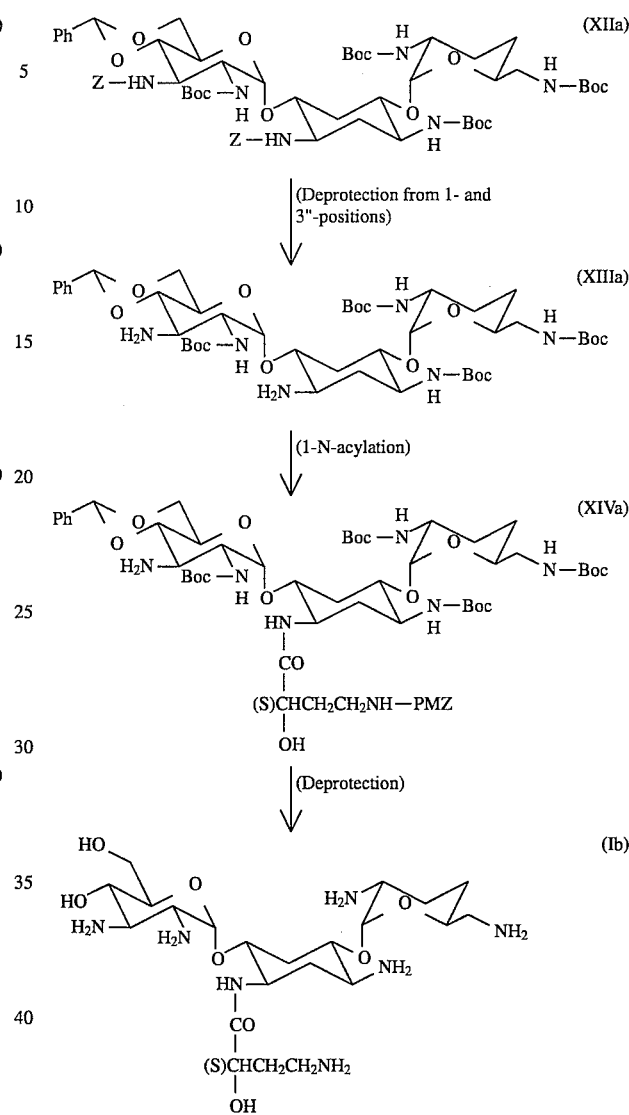

"Synthetic Process Chart C" given below briefly shows a step of the process according to the fifth aspect of this invention, where 2"-amino-2"-deoxydibekacin of formula (IIa) is synthesized using the compound of formula (IXa) which is obtained as an intermediate in "Synthetic Process Chart A" which shows a preferred embodiment for carrying out the process of the third aspect of this invention.

Synthetic Process Chart C

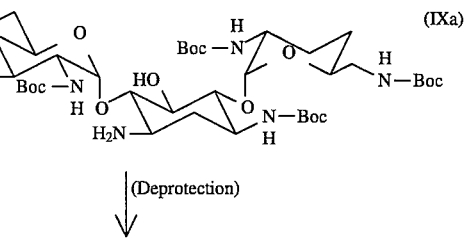

Synthetic Process Chart C -continued

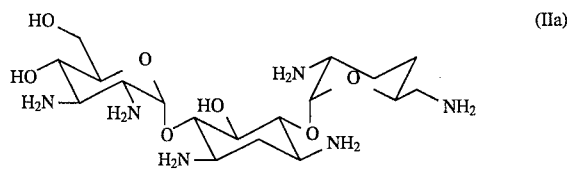

"Synthetic Process Chart D" given below briefly shows a step of the process according to the sixth aspect of this invention, where 2"-amino-5,2"-dideoxydibekacin of formula (IIb) is synthesized using the compound of formula (XIIIa) which is obtained as an intermediate in "Synthetic Process Chart B" above which shows a preferred embodiment for carrying out the process of the third aspect of this invention.

Synthetic Process Chart D

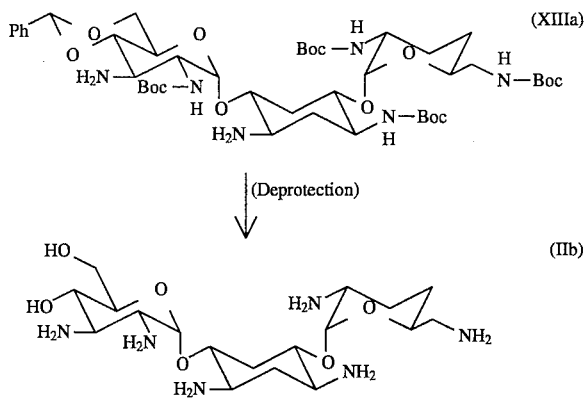

The following is some detailed descriptions about Synthetic Process Chart A above which illustrates a preferred embodiment for carrying out the process for the preparation of the compound of formula (Ia) i.e. 2"-amino-2"-deoxyarbekacin according to the third aspect of this invention.

3,2',6'-N-Tris(t-butoxycarbonyl)-dibekacin of formula (IIIa) (hereinafter simply referred to as 3,2',6'-N-tris(B-OC)dibekacin) which is to be used as the starting material is a partially amino-protected derivative of dibekacin which may be synthesized by acylating dibekacin with t-butoxycarbonyl chloride in the presence of zinc acetate as described in the specification of Japanese Patent Publication Sho-63-1319 or U.S. Pat. No. 4,297,485.

As depicted in Synthetic Process Chart A, the compound of formula (IVa), i.e. 1,3"-N-bis(benzyloxy-carbonyl)-3,2', 6'-N-tris(t-butoxycarbonyl)-dibekacin is produced by protecting in a usual manner each of the two amino groups at the 1- and 3"-positions of 3,2',6' -N-tris(BOC)dibekacin (IIIa) with an amino-protecting group which is removable by a deprotecting method different from that for the removal of BOC, and which is, for example, benzyloxycarbonyl group, one of aralkyloxycarbonyl groups. Subsequently, the two hydroxyl groups at the 4"- and 6"-positions of the compound (IVa) are protected simultaneously with a benzylidene group which is one of aralkylidene groups, whereby to form the compound of formula (Va), i.e. 4",6"-O-benzylidene-1,3"-N-bis (benzyloxycarbonyl)-3,2',6' -N-tris(t-butoxycarbonyl)-dibekacin.

The 2"-OH group of the compound (Va) is then converted into amino group. The conversion of the 2"-OH group into amino group may be achieved, for example, by a usual method of Pfitzner-Moffatt-for oxidation [B. P. Mundy and M. G. Ellerd, "Name Reactions and Reagents in Organic Synthesis", John Wiley & Sons, New York, p.162 (1988)], thus forming the 2"-keto derivatives of formula (VIa), i.e. 4",6"-O-benzylidene-1,3"-N-bis (benzyloxycarbonyl)-3,2', 6' -N-tris (t-butoxycarbonyl)-2"-deoxy-2"-oxodibekacin, followed by subjecting the compound (VIa) to a reductive amination known per se [for example, R. F. Borch et al., "J. Am. Chem. Soc." 93, 2897 (1971)] for the conversion of the 2"-oxo group into 2"-amino group. We have found that equatorial 2"-$NH_2$ group is preferentially formed by adopting this reductive amination. The said reductive amination reaction may be effected by reduction of the compound (VIa) with a hydride, for example, sodium cyanoborohydride in the presence of ammonium acetate.

Thus, there is produced the 2"-amino derivative of formula (VIIa), i.e. 2"-amino-4",6"-O-benzylidene-1,3" -N-bis (benzyloxycarbonyl)-3,2',6'-N-tris (t-butoxycarbonyl)-2"-deoxydibekacin.

Then, the 2"-amino group of the compound of formula (VIIa) is protected with BOC group as amino-protecting group to afford the compound of formula (VIIIa), i.e. 2"-amino-4",6"-O-benzylidene-1,3" -N-bis(benzyloxycarbonyl)-3,2',6',2"-N-tetrakis (t-butoxycarbonyl)-2"-deoxydibekacin. Subsequently, the 1- and 3"-benzyloxycarbonyl groups of the compound (VIIIa) are removed by hydrogenolysis in a usual manner to give the compound of formula (IXa), i.e. 2"-amino-4",6"-O-benzylidene-3,2'6',2"-N-tetrakis(t-butoxy-carbonyl)-2"-deoxydibekacin. The 1-amino group of the compound (IXa) is then acylated preferentially with (S)-4-amino-2-hydroxybutyric acid whose amino group has been protected with p-methoxybenzyloxycarbonyl group, by a known 1-N-acylating method. Subsequently, the resulting 1-N-acylated product of formula (XIa) is treated with aqueous trifluoroacetic acid or the like to remove the amino-protecting groups and the hydroxy-protecting groups all at once. The product thus obtained is purified by a column chromatography using a weak cation-exchange resin to yield 2"-amino-2"-deoxyarbekacin of formula (Ia) which has only one acylated-amino group at the 1-position as the object product.

Each of the reaction steps of Synthetic Process Chart A will be illustrated in more detail in Example 1 given later.

Some further explanation is now given on Synthetic Process Chart B. 5-Deoxy derivative of formula (XIIa), i.e. 2"-amino-2",6"-O-benzylidene-1,3 -N-bis(benzyloxy-carbonyl)-3,2',6',2"-N-tetrakis(t-butoxycarbonyl)-5,2"-dideoxydibekacin is prepared by converting the 5-OH group of the compound of formula (VIIIa) shown in the above Synthetic Process Chart A into a dithiocarbonate group ($H_3CSC(=S)O-$) and reducing said group with a hydride according to a known deoxygenation method [e.g. T. Hayashi et al., "Chem. Pharm. Bull.", 26, 1786, (1978)].

The 1-N-acylated product of formula (XIVa) is prepared by removing the benzyloxycarbonyl group from each of the protected 1- and 3"-amino groups of the compound of formula (XIIa) in the same manner as for the compound of formula (VIIIa) shown in Synthetic Process Chart A, to afford the compound of formula (XIIIa), i.e. 2"-amino-4",6"-O-benzylidene-3,2',6',2"-N-tetrakis(t-butoxycarbonyl)- 5,2"-dideoxydibekacin, followed by acylating the 1-amino group with (S)-4-amino-2-hydroxybutyric acid whose amino group has been protected by p-methoxybenzyloxycarbonyl group. The compound of formula (XIVa) thus obtained is then deprotected by hydrolysis with aqueous trifluoroacetic acid or another suitable acid to remove the benzylidene group and amino-protecting groups, thus affording the object compound, 2"-amino-5,2"-dideoxyarbekacin of formula (Ib).

Each of the reaction steps of Synthetic Process Chart B will be illustrated in more detail in Example 2 given below.

An explanation is now given on Synthetic Process Chart C. Thus, when the compound of formula (IXa) shown in Synthetic Process Chart A is subjected to conventional deprotecting reactions, 2"-amino-2"-deoxydibekacin of formula (IIa) is produced (see Example 3 given later).

Further, an explanation is given on Synthetic Process Chart D. Thus, when the compound of formula (XIIIa) shown in Synthetic Process Chart B is subjected to conventional deprotecting reactions, 2"-amino-5,2"-dideoxydibekacin of formula (IIb) is produced (see Example 4 given later).

As described in this specification hereinbefore, 2"-amino-2"-deoxydibekacin, 2"-amino-2"-deoxyarbekacin and their 5-deoxy derivatives which are hardly susceptible of the enzymatic phosphorylation at their 2"-position have now been provided according to this invention as the new antibiotics which are active-against methicillin-resistant *Staphylococcus aureus* (MRSA). On the other hand, we, the present inventors, have been aware of that as a modified 5-hydroxyl derivative of sisomicin which is one of the aminoglycosidic antibiotics containing deoxystreptamine moiety, there are known 5-epi-amino-5-deoxysisomicin and 5-epi-fluoro-5-deoxysisomicin represented by general formula (B)

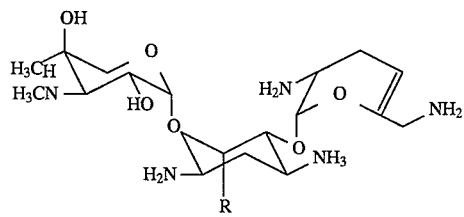

wherein R means an amino group for 5-epi-amino-5-deoxysisomicin or R means a fluorine atom for 5-epi-fluoro-5-deoxysisomicin, and that these 5-epi derivatives of sisomicin have good antibacterial activity (see P. J. L. Daniels et al "Aminoglycoside Antibiotics" edited by K. L. Reinhart, Jr. and T. Suami, pages 371–392 (1980), American Chemical Society, Washington).

We have recently found that 2"-amino-5,2"-dideoxy-arbekacin provided in the first aspect of this invention can exhibit broad and excellent antibacterial activity against a variety of gram-positive and gram-negative bacteria, including MRSA, but shows a higher acute toxicity to mice than that of 2"-amino-2"-deoxyarbekacin. Accordingly, we have made further studies in an attempt to provide another new arbekacin derivatives which are of reduced acute toxicity but show excellent antibacterial activity.

Thus, we have now studied chemical synthesis of 5-substituted-2"-amino-2"-deoxyarbekacins and succeeded in synthesizing 2"-amino-5,2"-dideoxy-5-epi-fluoroarbekacin and 2"-amino-5,2"-dideoxy-5-epi-aminoarbekacin represented by general formula (XVI) shown below. Moreover, it has been found that these new two derivatives of arbekacin having general formula (XVI) can strongly inhibit the growth of MRSA and further exhibit broad and effective antibacterial activity against a variety of gram-positive and gram-negative bacteria but have reduced toxicity to mammals.

According to a seventh aspect of this invention, therefore, there are provided a 5-substituted-2"-amino-2"-deoxyarbekacin represented by the following general formula (XVI)

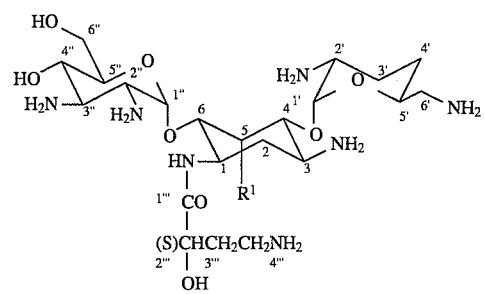

wherein $R^1$ means a fluorine atom or an amino group, and an acid addition salt thereof.

The compound of general formula (XVI) where $R^1$ means a fluorine atom is 2"-amino-5,2"-dideoxy-5-epi-fluoroarbekacin represented by the following formula (XVIa)

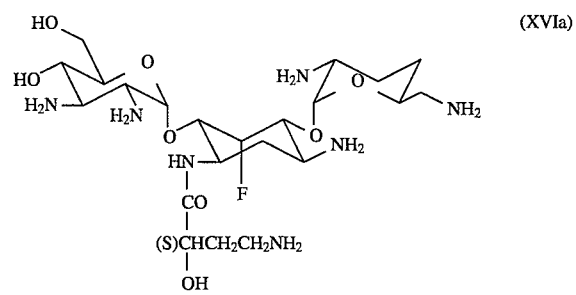

The compound of general formula (XVI) where $R^1$ means an amino group is 2"-amino-5,2"-dideoxy-5-epi-aminoarbekacin represented by the following formula (XVIb)

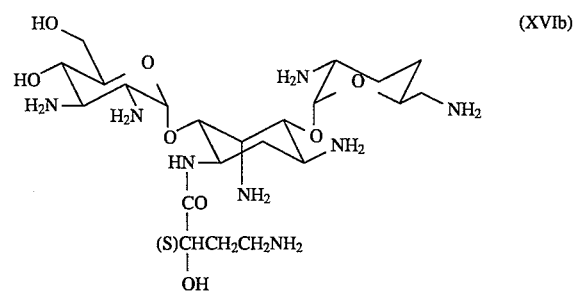

Physico-chemical properties of the new compounds provided according to the seventh aspect of this invention, namely 2"-amino-5,2"-dideoxy-5-epi-fluoroarbekacin of formula (XVIa) and 2"-amino-5,2"-dideoxy-5-epi-aminoarbekacin of formula (XVIb) are described below:

[1] 2"-Amino-5,2"-dideoxy-5-epi-fluoroarbekacin [Compound XVIa]

(1) Color and form: colorless powder (2) Molecular formula: $C_{22}H_{44}FN_7O_8$ (3) Mass spectrum (SI-MS): m/z 554(M+H)$^+$ (4) Melting point: 164°–171° C. (decomposed)

(5) Optical rotation: $[\alpha]_D^{20}$ +108° (c 1.0 $H_2O$)

(6) UV and visible ray-absorption spectra: no specific absorption (7) Infrared absorption spectrum (KBr): 3400, 1660 1600, 1490, 1400, 1350, 1130, 1060, 860 cm$^{-1}$ (8) $^1$H-NMR spectrum($D_2O$, pD 2): δ1.66 (1H, m, 4'ax-H), 1.85–1.99 (3H, m, 2ax-H, 4'eq-H, 3"-H), 2.00–2.11 (2H, m, 3'-$H_2$), 2.22 (1H, m, 3'''-H), 2.41(1H, m, 2eq-H), 3.11(1H, dd, J=7.7, 11.3 Hz, 6'-H), 3.19 (1H, t, 4''''-H), 3.28 (1H, dd, 6'-H), 3.61 (1H, m, 2'-H), 3.70 (1H, dd, J=9.7, 10.0 Hz, 4"-H), 3.77(1H, dd, J-12.3 Hz, 6"-H), 3.79(1H, t, J=11.3 Hz, 3"-H), 3.85(1H, m, 3-H), 3.90(1H, dd, J=3.9 Hz, 2"-H), 4.01(1H, d, 6"-H), 4.07 (1H, m, 5"-H), 4.12 (1H, m, 5'-H), 4.29 (1H, dd, J=10.8, 25.9 Hz, 4-H), 4.30–4.34 (2H, m, 1-H, 6-H), 4.35(1H, dd, J=4.0, 9.4 Hz, 2'''-H), 5.49(1H, d, J=3.4 Hz, 1'-H), 5.53(1H, d, J=3.9 Hz, 1"-H), 5.72(1H, d, J=51.0 Hz, 5-H)

(9) Solubility: easily soluble in water

(10) Distinction between basic, acidic and neutral substances in nature: basic substance

[2] 2"-Amino-5,2"dideoxy-5-epi-aminoarbekacin [Compound XVIb]

(1) Color and form: colorless powder (2) Molecular formula: $C_{22}H_{46}N_8O_8$ (3) Mass spectrum(FD-MS): m/z 551(M+H)$^+$ (4) Melting point: 192°–199° C. (decomposed)

(5) Optical rotation: $[\alpha]_D^{20}+102°$ (c 1.0, $H_2O$)

(6) UV and visible ray-absorption spectra: no specific absorption (7) Infrared absorption spectrum (KBr): 3420, 1650, 1590, 1480, 1400, 1350, 1120, 1040, 830 cm$^{-1}$ (8) $^1$H-NMR spectrum($D_2O$, pD2): δ1.71 (1H, m, 4'-ax-H), 1.92–2.07(3H, m, 2ax-H, 4' eq-H, 3'''-H), 2.10–2.15(2H, m, 3 '-$H_2$), 2.21 (1H, m, 3'''-H), 2.45(1H, dt, J=4.7, 13.3 Hz, 2eq-H), 3.19 (1H, t, J=6.9 Hz, 4 '''-H), 3.22(1H, dd, J=6.4 Hz, 6'-H), 3.34(1H, dd, J=3.6 Hz, 6'-H), 3.74(1H, m, 2'-H), 3.78–3.88(4H, m, 3-H, 3"-H, 4"-H, 6"-H), 3.93–3.95(2H, m, 4-H 2"-H), 4.03(1H, d, J=11, 1 Hz, 6"-H), 4.17(1H, ddd, 5'-H), 4.37(1H, dd, J=3.6, 9.4 Hz, 2'''-H), 4.46(1H, td, 1-H), 4.57(1H, br, 5-H), 4.59(1H, m, 5"-H), 4.68(1H, dd, J=3.3, 11.1 Hz, 6-H), 5.54(1H, d, J=3.3 Hz, 1'-H), 5.58(1H, d, J=2.2 Hz , 1"-H)

(9) Solubility: easily soluble in water

(10) Distinction between basic, acidic and neutral substances in nature: basic substance Similarly to the new arbekacin derivatives of general formula (I) according to the first aspect of this invention, 2,,-amino-5,2"-dideoxy-5-epi-fluoroarbekacin of formula (XVIa) and 2"-amino-5,2"-dideoxy-5-epi-aminoarbekacin of formula (XVIb) according to the seventh aspect of this invention can form their acid addition salts which include such those with a pharmaceutically acceptable inorganic acid, e.g. hydrochloric acid, sulfuric acid, phosphoric acid, nitric acid and the like or with a pharmaceutically acceptable organic acid, e.g. malic acid, citric acid, ascorbic acid, methanesulfonic acid and the like.

Biological properties of the new 5-substituted-2"-amino-2"-deoxyarbekacins provided according to the seventh aspect of this invention are next described.

(1) Antibacterial activities

Minimum growth inhibitory concentrations (MIC) of each of 2"-amino-5,2"-dideoxy-5-epi-fluoroarbekacin (Compound XVIa) and 2"-amino-5,2"-dideoxy-5-epi-aminoarbekacin (Compound XVIb) against various bacteria (18 strains) and against clinically isolated strains of MRSA (50 strains) were determined by standard serial dilution method on Müller-Hinton's agar medium (as estimated after cultivation at 27° C. for 18 hours), and the test results obtained are shown in TABLE 5 and TABLE 6, respectively.

TABLE 5

| | MIC. (μg/ml) | |
|---|---|---|
| Test organisms | Compound XVIa | Compound XVIb |
| Staphylococcus aureus FDA209P | 0.78 | ≦0.20 |
| S. aureus Smith | ≦0.20 | ≦0.20 |
| S. epidermidis 109 | 0.78 | 0.39 |
| Bacillus subtilis PCI219 | 0.39 | ≦0.20 |
| Escherichia coli NIHJ | 0.78 | 0.78 |
| E. coli K-12 ML1629 | 3.13 | 1.56 |
| E. coli K-12 LA290 R55 | 1.56 | 1.56 |
| E. coli JR66/W677 | 3.13 | 3.13 |
| Klebsiella pneumoniae PCI602 | 1.56 | 1.56 |
| Shigella dysenteriae JS1910 | 3.13 | 3.13 |
| Salmonella typhi T-63 | 0.78 | 0.78 |
| Proteus vulgaris OX19 | 1.56 | 1.56 |
| Providencia retteri GN311 | 1.56 | 1.56 |
| Serratia marcescens | 1.56 | 3.13 |
| Pseudomonas aeruginosa A3 | 0.78 | 0.39 |
| P. aeruginosa H9 | 3.13 | 3.13 |
| P. aeruginosa TI-13 | 1.56 | 1.56 |
| P. aeruginosa PST1 | 12.5 | 6.25 |

TABLE 6

| Test compound | Antibacterial MIC spectra (μg/ml) against 50 clinically isolated strains of MRSA | MIC$_{50}$ | MIC$_{90}$ |
|---|---|---|---|
| Compound XVIa | 0.39–3.13 | 0.78 | 1.56 |
| Compound XVIB | 0.39–1.56 | 0.78 | 1.56 |
| DKB (comparative) | ≦0.20–>100 | 50 | >100 |
| ABK (comparative) | ≦0.20–6.25 | 0.39 | 6.25 |

Note:
MIC$_{50}$ or MIC$_{90}$ represents the concentration of tested active compound at which 50% or 90% of the total numbers of the bacterial strains tested were inhibited from their growth. DKB denotes dibekacin, and ABK denotes arbekacin.

(2) Acute toxicity

50% Lethal dosages (LD$_{50}$, observations for two weeks) of the new compounds of general formula (XVI) according to the seventh aspect of this invention as estimated upon single intravenous administration to mice (ICR-strain, 4 weeks old, female) are as follows:

| | LD$_{50}$ |
|---|---|
| 2"-Amino-5,2"-dideoxy-5-epi-fluoroarbekacin (Compound XVIa) | >100 mg/kg |
| 2"-Amino-5,2"-dideoxy-5-epi-aminoarbekacin (Compound XVIb) | >100 mg/kg |

Based on the above elucidation of the biological properties of the new compounds of formulae (XVIa) and (XVIb) according to the seventh aspect of this invention, it has been proved that these new compounds of general formula (XVI) again not only inhibit strongly the growth of methicillin-resistant Staphylococcus aureus, but also have broad and highly effective antibacterial activities against gram-positive and gram-negative bacteria, including Pseudomonas aeruginosa and are of reduced toxicity to mammals.

The compound of formula (XVIa) and the compound of formula (XVIb) or acid addition salts thereof according to the seventh aspect of this invention may be formulated into various antibacterial compositions containing the said compound(s) as active ingredient by blending the same with pharmaceutically acceptable liquid or solid carrier(s) which may be used conventionally. Antibacterial compositions containing the compound of formulae (XVIa) or (XVIb) or their acid addition salt may be used primarily in various formulations for administration, including injections such as intravenous injections, oral compositions such as capsules, tablets, powder and granules, and others such as ointment, intrarectal agent, suppositories of oil-fat type, water-soluble suppositories, and the like. These various formulations may be prepared in any conventional manner with using conventional excipients, fillers, binders, wetting agents, disintegrators, surfactants, lubricants, dispersants, buffers, preservatives, dissolution aids, antiseptics, flavorings, indolent agents, and the like.

The 5-substituted-2"-amino-2"-deoxyarbekacins of general formula (XVI) according to the seventh aspect of this invention can be produced with using as a starting compound the new compound, 2"-amino-2"-deoxyarbekacin of formula (Ia) obtained in the first aspect of this invention described hereinbefore.

For the production of 2"-amino-5,2"-dideoxy-5-epi-fluoroarbekacin of formula (XVIa) according to the seventh aspect of this invention, there is provided in an eighth aspect of this invention a process for the preparation of 2"-amino-5,2"-dideoxy-5-epi-fluoroarbekacin of the following formula (XVIa)

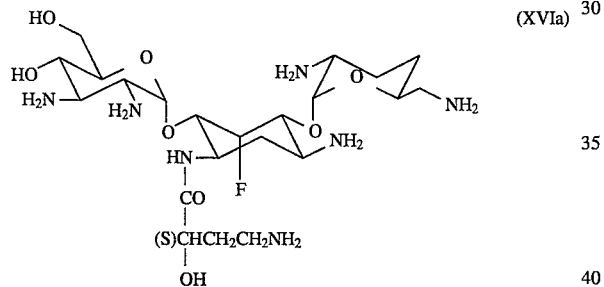

(XVIa)

which comprises the steps of:

protecting all the six amino groups of 2"-amino-2"-deoxyarbekacin of formula (XVII)

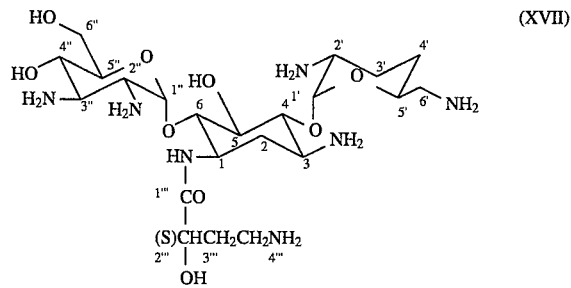

(XVII)

with an alkoxycarbonyl group which serves as an amino-protecting group readily removable by hydrolysis, followed by protecting the 4"-, 6"- and 2"'-hydroxyl groups of the resulting N-alkoxycarbonylated 2"-amino-2"-deoxyarbekacin through selective acylation of these hydroxyl groups with an alkanoyl group, thereby to produce from said 2"-amino-2"-deocyarbekacin, a 4",6",2"'-tri-O-acyl-3,2',6', 2",3",4"'-N-hexakis(alkoxycarbonyl)-2"-amino-2"-deoxyarbekacin represented by general formula (XVIIa)

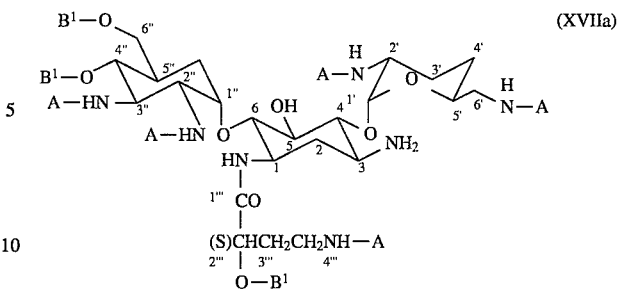

(XVIIa)

wherein A means an alkoxycarbonyl group as the amino-protecting group removable by hydrolysis and $B^1$ means a lower alkanoyl group as the hydroxyl-protecting group removable by hydrolysis;

then reacting a fluorination agent with the compound of formula (XVIIa) to introduce a fluorine atom in the axial direction into the 5-position of the same compound (XVIIa) and thereby to produce a 5-epi-fluoro derivative represented by the following general formula (XVIIIa)

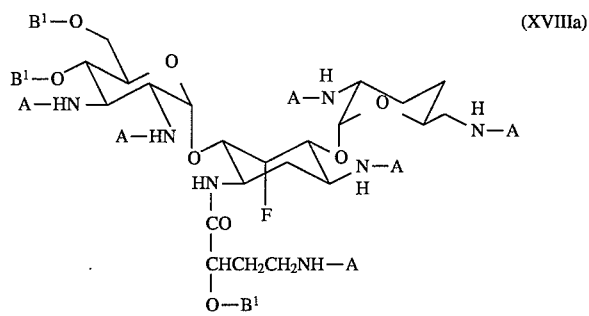

(XVIIIa)

wherein A means the amino-protecting group as defined above and $B^1$ means the hydroxyl-protecting group as defined above; and effecting the removal of the amino-protecting groups by acidic hydrolysis and the removal of the hydroxyl-protecting groups by alkaline hydrolysis from the compound of general formula (XVIIIa) to produce the compound of formula (XVIa).

Here, it is to be noted that the compound of formula (XVII) shown just above is identical to the compound of formula (Ia) given hereinbefore for the first aspect of this invention, that is, 2"-amino-2"-deoxyarbekacin.

The amino-protecting group (A) which may be available and introduced into the amino groups of the starting compound of formula (XVII) in the process of the eighth aspect of this invention includes a known alkoxycarbonyl group such as t-butoxycarbonyl group, as well as an aralkyloxycarbonyl group such as p-methoxybenzyloxycarbonyl group etc., which are readily removable by acidic hydrolysis. The introduction of such amino-protecting group into amino groups of the compound (XVII) may be effected by a conventional technique for protection of amino groups as known in the art of peptide chemistry. The acyl group, particularly an alkanoyl group ($B^1$) which may be available and introduced into some hydroxyl groups of the compound (XVII) includes an alkanoyl group containing 2–5 carbon atoms which is easily removable by alkaline hydrolysis. For instance, such a compound of general formula (XVIIa) where A is the amino-protecting group as set out above but $B^1$ is still a hydrogen atom, for example, a 3,2',6',2",3",4"'-N-hexakis(alkoxycarbonyl)-2"-amino-2"-deoxyarbekacin may be reacted with an acylating agent, e.g. acetyl anhydride in pyridine so that the acyl group, e.g. acetyl group is preferentially and efficiently introduced into each of the three hydroxyl groups at the 4"-, 6"- and 2'''-positions of the compound employed, whereby there is formed such a compound of general formula (XVIIa) where A is the amino-protecting group, B¹ is the hydroxyl-protecting acyl group as introduced but the 5-hydroxyl group remains unprotected, for example, a 4",6",2'''-tri-O-acyl-3,2',6',2",3''',4'''-N-hexakis(alkoxycarbonyl)-2"-amino-2"-deoxyarbekacin.

For replacement of the 5-hydroxyl group of the compound of formula (XVIIa) by a fluorine atom, this compound is reacted with a known fluorination agent, for example, a dialkylsulfur trifluoride such as dimethylsulfur trifluoride or a dialkylaminosulfur trifluoride such as diethylaminosulfur trifluoride (usually abbreviated as DAST) and the like. This fluorination reaction can be conducted in dichloromethane in the presence of pyridine at ambient temperature.

This fluorination reaction gives the compound of general formula (XVIIIa). The latter compound is then subjected to a conventional method for removal of the amino-protecting group by acidic hydrolysis to remove the amino-protecting groups (A) therefrom. The resulting N-unprotected product is subsequently subjected to a conventional method for removal of the hydroxyl-protecting groups by alkaline hydrolysis to remove the hydroxyl-protecting groups (B¹) therefrom. There is thus produced the compound of formula (XVIa) as aimed at in the eighth aspect of this invention.

For the production of 2"-amino-5,2"-dideoxy-5-epi-aminoarbekacin of formula (XVIb) according to the seventh aspect of this invention, there is provided in a ninth aspect of this invention a process for the preparation of 2"-amino-5,2"-dideoxy-5-epi-aminoarbekacin of the following formula (XVIb)

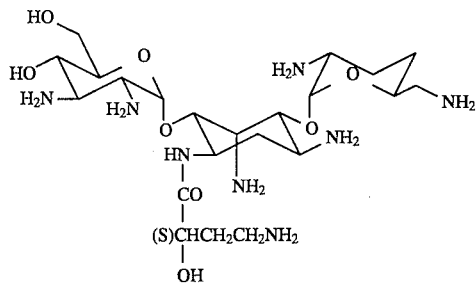

which comprises the steps of:

alkylsulfonylating the 5-hydroxyl group of a 4",6", 2'''-tri-O-acyl-3,2',6',2",3''',4'''-N-hexakis(alkoxycarbonyl)-2"-amino-2"-deoxyarbekacin represented by general formula (XVIIa)

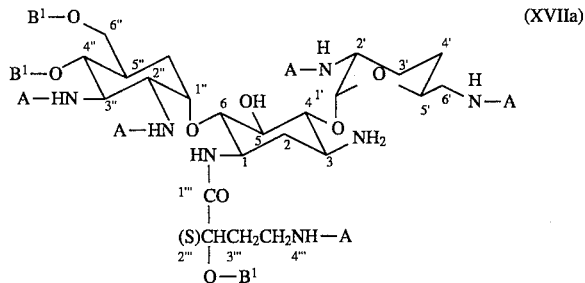

wherein A means an alkoxycarbonyl group as an amino-protecting group and B¹ means a lower alkanoyl group as a hydroxyl-protecting group, to form a 5-O-alkylsulfonylated derivative represented by the following general formula (XVIIb)

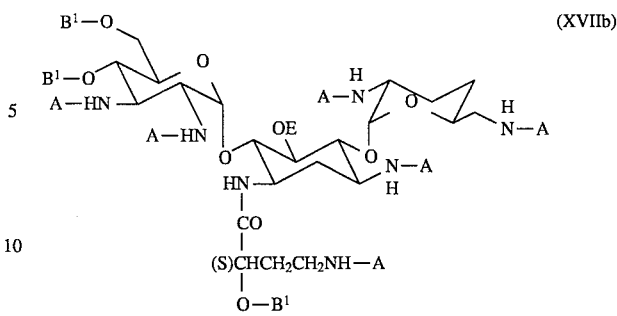

wherein A and B¹ have the same meanings as defined above and E means an alkylsulfonyl group;

then reacting an azidation agent with the alkyl-sulfonyloxy group at the 5-position of the compound of general formula (XVIIb) to introduce an azido group in the axial direction into the 5-position of the same compound and thereby to produce a 5-epi-azido derivative represented by general formula (XVIIIb)

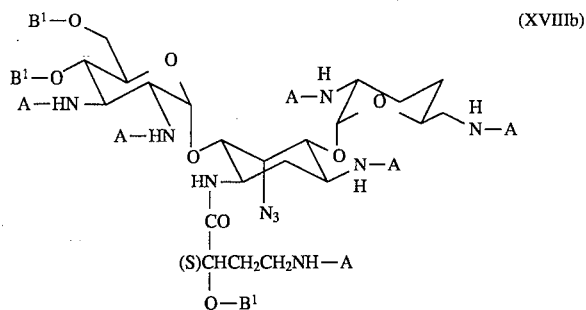

wherein A and B¹ have the same meanings as defined above;

subsequently hydrogenating the compound of general formula (XVIIIb) to form a 5-epi-amino derivative represented by the following general formula (XVIIIc)

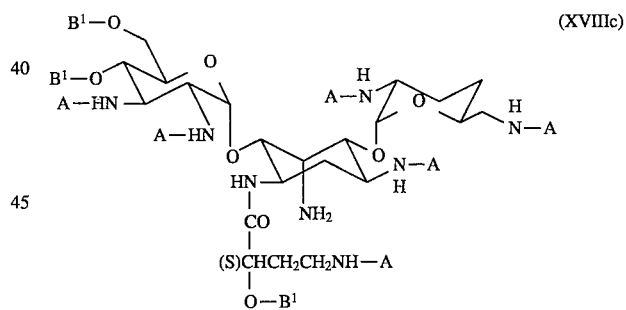

wherein A and B¹ have the same meanings as defined above, and effecting the removal of the amino-protecting groups by acidic hydrolysis and the removal of the hydroxyl-protecting groups by alkaline hydrolysis from the compound of general formula (XVIIIc) to produce the compound of formula (XVIb).

In respect of the process according to the ninth aspect of this invention, the amino-protecting group (A) available in the starting compound of general formula (XVIIa) may include a known alkoxycarbonyl group such as t-butoxycarbonyl group and an aralkyloxycarbonyl group such as p-methoxybenzyloxycarbonyl group which are readily removable by acidic hydrolysis. The hydroxyl-protecting acyl group (B¹) available in the same compound (XVIIa) may include a $C_{2-C_5}$ alkanoyl group which is readily removable by alkaline hydrolysis. These protective groups (A and B¹) present in the compound (XVIIa) may respectively be the same as the amino-protecting group (A) and the hydroxyl-protecting group (B) present in the compound of general formula (XVIIa) as employed in the process of the eighth aspect of this invention.

In the process of the ninth aspect of this invention, the compound of general formula (XVIIa) is used and the 5-hydroxyl group of this compound is first alkylsulfonylated, for example, methanesulfonylated (i.e. mesylated) in a known manner to give a 5-O-alkylsulfonylated derivative of general formula (XVIIb). This derivative (XVIIb) is then reacted with a known azidation reagent such as sodium azide to effect a nucleophilic substitution reaction for replacing the 5-alkylsulfonyloxy group by azido group with accompanying inversion of the configuration of the 5-substituent, whereby there is formed the 5-epi-azido derivative of general formula (XVIIIb). Subsequently, in order to convert the 5-azido group into amino group, the compound of general formula (XVIIIb) is subjected to a catalytic reduction in a known manner using Ranney nickel as catalyst. In this way, the 5-epi-amino derivative of general formula (XVIIIc) is produced.

The 5-epi-amino derivative of general formula (XVIIIc) as produced from the above step of catalytic reduction is then subjected to a conventional method for removal of the amino-protecting group by acidic hydrolysis to remove the amino-protecting groups (A) therefrom. The resulting N-unprotected product is subsequently subjected to a conventional method for removal of the hydroxyl-protecting group by alkaline hydrolysis to remove the hydroxyl-protecting groups ($B^1$) therefrom. There is thus produced the compound of formula (XVIb) as aimed at in the ninth aspect of this invention.

Furthermore, an antibacterial composition which contains a new compound of this invention having the formula (Ia), (Ib), (IIa), (IIb), (XVIa) or (XVIb) given hereinbefore or an acid addition salt thereof as the active ingredient may be prepared by mixing the active compound with one or more known liquid or solid carrier(s) of various kinds in appropriate proportions, and optionally further incorporating one or more known additives into the composition. The dosage of the new compound of this invention when administered will depend on the nature of diseases to be treated, conditions of the diseases and other different factors, but its optimum dosage can be decided by ordinary and appropriate, preliminary tests.

According to a tenth aspect of this invention, therefore, there is provided an antibacterial composition comprising 2"-amino-2"-deoxyarbekacin, 2"-amino-5,2"-dideoxyarbekacin or an acid addition salt thereof as active ingredient, in combination with a pharmaceutically acceptable carrier for the active ingredient.

According to a further aspect of this invention, there is provided an antibacterial composition comprising 2"-amino-2"-deoxydibekacin, 2"-amino-5,2"-dideoxydibekacin or an acid addition salt thereof as active ingredient, in combination with a pharmaceutically acceptable carrier for the active ingredient.

According to further another aspect of this invention, there is provided an antibacterial composition comprising 2"-amino-5,2"-dideoxy-5-epi-fluoroarbekacin, 2"-amino-5, 2"-dideoxy-5-epi-aminoarbekacin or an acid addition salt thereof as active ingredient, in combination with a pharmaceutically acceptable carrier for the active ingredient.

This invention further includes use of 2"-amino-2"-deoxyarbekacin, 2"-amino-5,2"-dideoxyarbekacin, 2"-amino-5,2"-dideoxy-5-epi-fluoroarbekacin, 2"-amino-5, 2"-dideoxy-5-epi-aminoarbekacin, 2"-amino-2"-deoxydibekacin, 2"-amino-5,2"-dideoxydibekacin or an acid addition salt thereof in the manufacture of an antibacterial composition.

The first to sixth aspects of this invention are next illustrated with reference to the following Examples 1–4 to which this invention is not limited.

EXAMPLE 1

Synthesis of 2"-amino-2"-deoxyarbekacin (Compound Ia)

(1) 4",6"-O-Benzylidene-1,3"-N-bis(benzyloxycarbonyl)-3,2',6' -N-tris (t-butoxycarbonyl)-dibekacin (Compound Va):

3,2',6'-N-tris (t-butoxycarbonyl)-dibekacin (Compound IIIa) (9.02 g; 12.0 mmol), which is described in the specification of Japanese Patent Publication Sho-63-1319 or U.S. Pat. No. 4,297,485, was dissolved in N,N-dimethyl-formamide (DMF) (50 ml). To the resulting solution were added pyridine (10 ml) and N-(benzyloxycarbonyl)-succinimide (6.28 g) and the reaction was conducted at room temperature for 4 hours (for benzyloxycarbonylation of the 1- and 3"-amino groups). The resulting reaction solution was concentrated under a reduced pressure, followed by addition of water, and the precipitate thus formed was washed with water and ethyl ether to afford 1,3" -N-bis (benzyloxycarbonyl)-3,2',6'-N-tris(t-butoxycarbonyl)-dibekacin (9.90 g) (Compound IVa). FD-MS m/z 1020 (M+H)$^+$.

The 1,3"-N-bis (benzyloxycarbonyl) derivative obtained (4.98 g) was dissolved in DMF, and to the solution were added benzaldehyde dimethylacetal (3 ml) and anhydrous p-toluenesulfonic acid (200 mg). The resultant mixture was heated at 40° C. under a reduced pressure of 20 mm Hg with stirring for 1 hour to conduct the reaction (for 4", 6"-O-benzylidenation). The resulting reaction solution was extracted with chloroform (300 ml) added and the extract was washed with a saturated aqueous sodium hydrogen carbonate solution (50 ml) and with a 10% aqueous sodium chloride solution (50 ml) and then concentrated to dryness. The residue was reprecipitated from a hot mixture of tetrahydrofuran (THF) and ethyl acetate, affording the titled compound (3.88 g). $[\alpha]_D^{20}$+50° (c 1.2, DMF).

(2) 2"-Amino-4",6"-O-benzylidene-1,3" -N-bis (benzyloxy-carbonyl)-3,2',6',2"-N-tetrakis (t-butoxycarbonyl)-2"-deoxy-dibekacin (Compound VIIIa):

The compound (2.95 g) obtained in the above item (1) was dissolved in anhydrous dimethylsulfoxide (DMSO) (13 ml), to which pyridinium trifluoroacetate (250 mg) was then added. To the resulting solution, a solution of dicyclohexylcarbodiimide (1.68 g) in benzene (19 ml) was added, and the mixture obtained was stirred at room temperature overnight to conduct the oxidation reaction intended. A solution of oxalic acid dihydrate (685 mg) in dioxane (2.5 ml) was added dropwise to the resulting reaction solution, and the mixture obtained was stirred at room temperature for 30 minutes. The precipitate thus formed was filtered off and the filtrate was extracted with chloroform (180 ml) added. The extract was washed with a saturated aqueous sodium hydrogen carbonate solution (100 ml) and a 10% aqueous sodium chloride solution (200 ml) and then concentrated to dryness to afford the 2"-keto derivative, more specifically 4",6"-O-benzylidene-1,3" -N-bis(benzyloxycarbonyl)-3,2',6' -N-tris(t-butoxycarbonyl)-2"-deoxy-2"-oxodibekacin (Compound VIa) (3.35 g).

The 2"-keto compound thus prepared was dissolved in anhydrous methanol (100 ml), to which ammonium acetate (3.7 g) and sodium cyanoborohydride (673 mg) were added in order, and the mixture obtained was stirred at room temperature overnight to effect the reductive amination reaction. The resulting reaction solution was extracted with chloroform (300 ml) added, and the extract was washed with water, a saturated agueous sodium hydrogen carbonate solution and a 10% aqueous sodium chloride solution (100 ml each), successively, and then concentrated. Thereafter, the concentrate was purified by passing through a silica gel column (Wako gel C-300, a product of Wako Junyaku Kogyo K.K.; with diameter of 40 mm and height of 70 cm), eluting with chloroform-methanol (40:1), then with chloroform-methanol (20:1), collecting fractions containing the 2"-aminated derivative, more specifically 2"-amino-4", 6"-O-benzylidene-1,3"-N-bis (benzyloxycarbonyl)-3,2',6'-N-tris(t-butoxycarbonyl)-2"-deoxydibekac in (Compound VIIa) (which shows a value of Rf=0.16 when developed with chloroform-methanol (20:1) in the silica gel thin layer chromatography), and concentrating the fractions collected to dryness (775 mg).

The residue obtained was dissolved in a mixture of THF-methanol (1:1) (26 ml), to which were then added triethylamine (0.1 ml) and di-t-butyl dicarbonate (0.3 ml), and the resulting mixture was allowed to stand overnight at room temperature (for t-butoxycarbonylation reaction of the 2"-amino group). The resultant reaction solution was concentrated to dryness and the residue was purified by chromatography on a silica gel column (with diameter of 22 mm and height of 18 cm) as developed with chloroform-methanol (20:1), to afford the titled compound (752 mg). FD-MS m/z 1207 (M+H)$^+$ $[\alpha]_D^{20}$ +33° (c 1 CHCl$_3$).

(3) 2"-Amino-4",6"-O-benzylidene-3,2',6',2" -N-tetrakis-(t-butoxycarbonyl)-2"-deoxydibekacin (Compound IXa)

The compound (730 mg) obtained in the above item (2) was dissolved in a mixture (1:19) of 88% formic acid and methanol (40 ml), to which was then added 10% palladium-carbon (1.45 g) in an argon atmosphere, and the resulting admixture was subjected to hydrogenolysis (for 2 hours) to remove the benzyloxycarbonyl group from each of the 1- and 3"-amino groups. The reaction solution obtained was filtered, followed by concentrating to dryness to yield the titled compound (491 mg).

(4) 2"-Amino-2"-deoxyarbekacin (Compound Ia)

The compound (246 mg) obtained in the above item (3) was dissolved in THF (6 ml), to which was added triethylamine (35 μl). To the resulting solution was added a solution of an active ester which was prepared by adding N-hydroxysuccinimide (33 mg) and dicyclohexylcarbodiimide (61 mg) to (S)-4-(p-methoxybenzyloxycarbonylamino)-2-hydroxybutyric acid (81 mg) in THF (1.4 ml). The reaction mixture was agitated overnight at 5°–20° C. to effect the reaction. The resulting reaction solution was filtered to remove a small amount of insoluble matters and the filtrate was concentrated to dryness. The residue obtained was dissolved in chloroform (6 ml) and the solution was washed with a saturated aqueous sodium hydrogen carbonate solution (2 ml), then with a 10% aqueous sodium chloride solution (2 ml) and then concentrated to dryness. The residue obtained (269 mg) was purified by chromatography on a silica gel column (with diameter of 22 mm and height of 36 cm) as eluted first with chloroform, and then with a mixture (20:1) of chloroform and methanol. 1-N-[(S)-4-(p-methoxybenzyloxycarbonylamino)-2-hydroxybutyryl]-2" -amino-4",6"-O-benzylidene-3,2',6',2" -N-tetrakis(t-butoxy-carbonyl)-2"-deoxydibekacin (Compound XIa) (139 mg) was obtained as the 1-N-acylated product.

This compound was dissolved in a 90% trifluoroacetic acid (2.8 ml) and the solution was allowed to stand at room temperature for 1 hour to effect the removal of the benzylidene group, the removal of the t-butoxycarbonyl group and the removal of the p-methoxybenzyloxycarbonyl group (for the deprotections). Then, the resulting reaction solution was concentrated to dryness and washed with ether (9 ml). The residue was purified by dissolving in a small amount of water and passing the aqueous solution through a column of Amberlite CG-50 (NH$_4^+$form, 25 ml, a product of Rohm & Haas Company, U.S.A.), followed by washing the column with water (40 ml) and by gradiently eluting with 0.1~1.5M aqueous ammonia solutions. Thus, the object product, 2"-amino-2"-deoxyarbekacin (38 mg) was yielded.

EXAMPLE 2

Synthesis of 2"-amino-5,2"-dideoxyarbekacin (Compound Ib) (1) 2"-Amino-4",6"-O-benzylidene-1,3" -N-bis (benzyloxy-carbonyl)-3,2',6',2"-N-tetrakis (t-butoxycarbonyl)-5,2" -dideoxydibekacin (Compound XIIa):

The compound (VIIIa) (184 mg) obtained in EXAMPLE 1 (2) above was dissolved in DMSO (1.6 ml), to which was then added carbon disulfide (0.8 ml). To the resulting mixture under vigorously stirring, an aqueous 8M NaOH (0.6 ml) was added dropwise, and after continuing the stirring at room temperature for 30 minutes, methyl iodide (1.6 ml) was added thereto. The resulting reaction mixture was further stirred for 2 hours. The reaction solution obtained was then concentrated to dryness and the residue was dissolved in chloroform (15 ml) and the resulting solution was washed with water (15 ml) and then concentrated to dryness. The resultant residue was purified by chromatography on a silica gel column (diameter of 22 mm and height of 25 cm) as eluted with chloroform first and then with a mixture (50:1) of chloroform and methanol. The 5-O-(methylthio)thiocarbonyl derivative of said compound (VIIIa) (123 mg) was obtained. FD-MS m/z 1297 (M+H)$^+$.

The 5-O-(methylthio)thiocarbonyl derivative (180 mg) was dissolved in toluene (4 ml), to which were then added tributyltin hydride (0.18 ml) and α,α'-azobisisobutyronitrile (5 mg), and the mixture was heated at 110° C. in argon stream for 50 minutes to effect the reaction intended. Hexane was added to the reaction solution obtained and the precipitate as deposited was separated centrifugally and then purified by chromatography on a silica gel column (diameter of 16 mm and height of 17 cm) as eluted with chloroform first and then with a mixture (50:1) of chloroform and methanol. The titled compound (154 mg) was afforded. FD-MS m/z 1191 (M$^+$), $[\alpha]_D^{20}$ +37° (c 1.3 CHCl$_3$).

(2) 2"-Amino-4",6"-O-benzylidene-3,2',6',2" -N-tetrakis-(t-butoxycarbonyl)-5,2"-dideoxydibekacin (Compound XIIIa):

The compound (149 mg) obtained in the above item (1) was dissolved in a mixture (1:19) of 88% formic acid and methanol (11.2 ml), and the resulting solution was subjected to hydrogenolysis (for 2.5 hours) in an argon atmosphere in the presence of a 10% palladium-carbon (520 mg) to remove the benzyloxycarbonyl groups from the 1- and 3"-amino groups. The reaction solution obtained was filtered and the filtrate was concentrated to dryness, yielding the titled compound (96 mg). FD-MS m/z 923 (M+H)$^+$.

(3) 2"-Amino-5,2"-dideoxyarbekacin (Compound Ib):

The compound (93 mg) obtained in the above item (2) was dissolved in THF (3 ml), to which was then added triethylamine (15 μl). To the solution obtained was added a solution of an active ester which was prepared by adding N-hydroxysuccinimide (15 mg) and dicyclohexylcarbodiimide (28 mg) to 4-(p-methoxybenzyloxycarbonylamino)-2-hydroxybutyric acid (37 mg) in THF (1.2 ml). The resulting reaction mixture was agitated at −15°–20° C. overnight to conduct the reaction and was filtered to remove a small amount of insoluble matters. The filtrate was concentrated to dryness. The residue obtained was dissolved in chloroform (6 ml) and the solution was washed with a saturated aqueous sodium hydrogen carbonate solution (2 ml) and a 10% aqueous sodium chloride solution (2 ml), in order, and concentrated to dryness. The resultant residue (100 mg) was then purified by chromatography on a silica gel column (diameter of 16 mm and height of 25 cm) as eluted with a mixture of chloroform and methanol (30:1). There was afforded 1-N-[(S)-4-(p-methoxybenzyloxycarbonylamino)-2 -hydroxybutyryl]-2"-amino-4",6"-O-benzylidene-3,2',6',2" -N-tetrakis(t-butoxycarbonyl)-5,2"-dideoxydibekacin (Compound XIVa) (81 mg) as the 1-N-acylated product.

The compound thus obtained was dissolved in trifluoroacetic acid (1.8 ml) and the solution was allowed to stand at room temperature for 1 hour. The resulting reaction solution was concentrated to dryness and then the residue was washed with ethyl ether (9 ml). The washed residue was dissolved in a small amount of water, and the aqueous solution was passed through a column of Amberlite CG-50 (NH$_4$+ form, 18 ml) for purification. The column was then washed with water (40 ml) and eluted gradiently with 0.1~1.5M aqueous ammonia. 2"-Amino-5,2"-dideoxyarbekacin (27 mg) was obtained as the object product.

EXAMPLE 3

Synthesis of 2"-amino-2"-deoxydibekacin (Compound IIa)

2 "-Amino-4",6"-O-benzylidene-3,2',6',2" -N-tetrakis-(t-butoxycabonyl)-2"-deoxydibekacin (Compound IXa) (38 mg) as described in EXAMPLE 1 (3) above was deprotected by treating with a 90% trifluoroacetic acid in the same manner as in EXAMPLE 1 (4) above, and the deprotected product was purified by chromatography on a column of Amberlite CG-50. 2"-Amino-2"-deoxydibekacin (16 mg) was obtained as the object product.

EXAMPLE 4

Synthesis of 2"-amino-5,2"-dideoxydibekacin (Compound IIb)

2"-Amino-4",6"-O-benzylidene-3,2',6',2" -N-tetrakis-(t-butoxycarbonyl)-5,2"-dideoxydibekacin (Compound XIIIa) (61 mg) as described in EXAMPLE 2 (2) above was deprotected by treating with a 90% trifluoroacetic acid in the same manner as in EXAMPLE 1 (4) above, and the unprotected product was purified by chromatography on a column of Amberlite CG-50. 2"-Amino-5,2"-dideoxydibekacin (21 mg) was obtained as the object product.

The seventh to ninth aspects of this invention are now illustrated with reference to the following Examples 5–6 to which this invention is not limited.

EXAMPLE 5

Synthesis of 2"-amino-5,2"-dedeoxy-5-epi-fluoroarbekacin (Compound XVIa)

(1) Production of 4",6",2'"-tri-O-acetyl-3,2',6',2",3",4'" -N-hexakis(t-butoxycarbonyl)-2"-amino-2"-deoxyarbekacin (Compound XVIIa-1):

2"-Amino-2"-deoxyarbekacin (400 mg) (Compound Ia) as prepared in EXAMPLE 1 above was dissolved in a mixture of water (4 ml), methanol (6 ml) and dioxane (1 ml), and to the resulting solution were added triethylamine (0.1 ml) and di-t-butyl dicarbonate (1.2 ml), followed by agitating the resultant mixture at 35° C. for 26 hours. The reaction solution obtained was concentrated under reduced pressure to dryness, and the residue was dissolved in pyridine (12 ml) to which acetic anhydride (2.4 ml) was then added under ice-cooling. The mixture obtained was agitated at room temperature for 3 hours and the resultant reaction solution containing the titled compound formed was added with water (0.5 ml) and then concentrated under reduced pressure to dryness. The residue was dissolved in chloroform (60 ml) and the solution obtained was washed three times with 12 ml-portions of a 5% aqueous sodium hydrogen carbonate solution and once with 12 ml of a 10% aqueous sodium chloride solution.

The washed solution in chloroform was dried over anhydrous sodium sulfate and concentrated under reduced pressure. The concentrate obtained was purified by chromatography on a silica gel column as developed first with chloroform and then with chloroform-methanol (40:1). Thus, there was afforded 4",6",2'"-tri-O-acetyl-3,2',6',2",3", 4'" -N-hexakis(t-butoxycarbonyl)-2"-amino-2"-deoxyarbekacin (Compound XVIIa-1) (840 mg). FD-MS m/z 1277(M$^+$), [α]$_D^{20}$ 41° (c 1.3, CHCl$_3$).

(2) Production of 4",6",2'"-tri-O-acetyl-3,2',6',2",3" ,4'"-N-hexakis (t-butoxycarbonyl)-2"-amino-5,2 "-dideoxy-5-epi-fluoroarbekacin (Compound XVIIIa-1):

A solution in dichloromethane (3 ml) of Compound (XVIIa-1) (160 mg) obtained in the above item (1) was added into a solution of diethylaminosulfur trifluoride (0.078 ml) in a mixture of dichloromethane (2.4 ml) and pyridine (0.16 mi) under ice-cooling. The mixture so obtained was subsequently stirred at room temperature for 2 hours. The resulting reaction solution containing the titled compound as produced was added with chloroform (4 ml) and then washed twice with 2 ml-portions of a saturated aqueous sodium hydrogen carbonate solution, once with 2 ml of a 5% aqueous sodium hydrogen sulfate solution and then once with 2 ml of water.

The washed solution in the organic solvents was dried over anhydrous sodium sulfate and concentrated under reduced pressure, and the residue obtained was purified by chromatography on a silica gel column as developed first with chloroform and then with chloroform-acetone (4:1), to afford the titled compound (119 mg). FD-MS m/z 1280 (M+H)$^+$, [α]$_D^{20}$+29° (c 1.2, CHCl$_3$).

(3) Production of 2"-amino-5,2"-dideoxy-5-epi-fluoroarbekacin (Compound XVIa):

The compound (120 mg) obtained in the above item (2) was dissolved in methanol (1.8 ml), to which was then added 1N sodium methylate in methanol (0.068 ml). The mixture obtained was stirred at room temperature for 1 hour, and the resulting reaction solution was neutralized by addition of a cation-exchange resin, Dowex 50W (H⁺ form) and then concentrated under reduced pressure. To the residue obtained was added 90% trifluoroacetic acid (1 ml) under ice-cooling, followed by stirring the mixture for 1.5 hours.

The resulting reaction solution contained the above titled compound produced as the unprotected product. This reaction solution was concentrated under reduced pressure and the concentrated solution was mixed with water (1 ml), followed by concentrating the mixture to dryness. The solid residue was taken up into water (3 ml) and the aqueous solution obtained was washed three times with 0.6 ml-portions of chloroform. The aqueous phase so washed was concentrated under reduced pressure and then the concentrate was charged into a cation-exchange resin, Amberlite CG-50 ($NH_4^+$ form, 10 ml) for adsoption of the titled compound by the resin. The resin column was then washed with water (20 ml) and then subjected to gradient elution with 0.2M to 0.8M aqueous ammonia for isolation and purification of the titled compound. 2"-Amino-5,2"-dideoxy-5-epi-fluoroarbekacin (Compound XVIa) was obtained in a yield of 27 mg.

EXAMPLE 6

Synthesis of 2"-amino-5,2"-dideoxy-5-epi-aminoarbekacin (Compound XVIb)

(1) Production of 4",6",2'"-tri-O-acetyl-3,2',6',2",3"',4"'-N-hexakis(t-butoxycarbonyl)-2"-amino-5,2" -dideoxy-5-epi-azidoarbekacin (Compound XVIIIb-1):

4",6",2'"-tri-O-acetyl-3,2',6',2",3"',4"' -N-hexakis-(t-butoxycarbonyl)-2"-amino-2"-deoxyarbekacin (Compound XVIIa-1) (235 mg) as obtained in EXAMPLE 5 (1) above was dissolved in dichloromethane (10 ml), to which was then added dimethylaminopyridine (674 mg) and further added methanesulfonyl chloride (0.214 ml) under ice-cooling. The mixture so obtained was stirred at room temperature for 16 hours to effect the mesylation. After this reaction, the resulting reaction solution was mixed with chloroform (15 ml), followed by washing three times with 5 ml-portions of a 5% aqueous potassium hydrogen sulfate solution and once with a 10% aqueous sodium chloride solution. The washed organic phase was dried over anhydrous sodium sulfate and then concentrated under reduced pressure.

The residue obtained was dissolved in dimethylformamide (4.8 ml), and to the resulting solution was added sodium azide (127 mg). The mixture obtained was heated at 120° C. for 3 hours under agitation. The resulting reaction solution containing the above titled compound as produced was concentrated under reduced pressure, and the residue was dissolved in chloroform (25 ml). The solution obtained was washed three times with 5 ml-portions of a 10% aqueous sodium chloride solution and the washed organic phase in chloroform was then dried over anhydrous sodium sulfate and concentrated under reduced pressure. The resulting residue was purified by chromatography on a silica gel column as developed first with chloroform and then with chloroform-methanol (10:1), so that the titled compound (233 mg) was afforded FD-MS m/z 1303 (M+H)⁺, $[\alpha]_D^{20}$+33° (c 1.1, CHCl₃).

(2) Production of 4",6",2'"-tri-O-acetyl-3,2',6',2",3"',4"' -N-hexakis(t-butoxycarbonyl)-2"-amino-5,2"-dideoxy-5-epi-aminoarbekacin (Compound XVIIIc-1):

The compound (140 mg) obtained in the above item (1), namely Compound (XVIIIb-1), was dissolved in methanol (6 ml) and then subjected to hydrogenation under a normal pressure for 3 hours in the presence of Ranney-nickel as catalyst. The resulting reaction solution was filtered to remove the catalyst, and the filtrate was concentrated under reduced pressure. The residue obtained was purified by chromatography on a silica gel column as developed first with chloroform-acetone (4:1) and then with chloroform-methanol (20:1), so that the above titled compound (89 mg) was obtained. FD-MS m/z 1277 (M+H)⁺, $[\alpha]_D^{20}$+43° (c 1.1, CHCl₃).

(3) Production of 2"-amino-5,2"-dideoxy-5-epi-aminoarbekacin (Compound XVIb):

The compound (87 mg) obtained in the above item (2), namely Compound (XVIIIc-1), was dissolved in methanol (1.8 ml) and then subjected to the deprotecting treatments with sodium methylate and with trifluoroacetic acid in the same manner as in the above procedures of EXAMPLE 5 (3) above. The unprotected product so obtained was purified by chromatography on a column of Amberlite CG-50 resin ($NH_4^+$ form, 10 ml) to give the above titled compound (Compound XVIb), namely 2"-amino-5,2"-dideoxy-5-epi-aminoarbekacin (28 mg).

We claim:

1. 2"-Amino-5,2"-dideoxyarbekacin having the formula

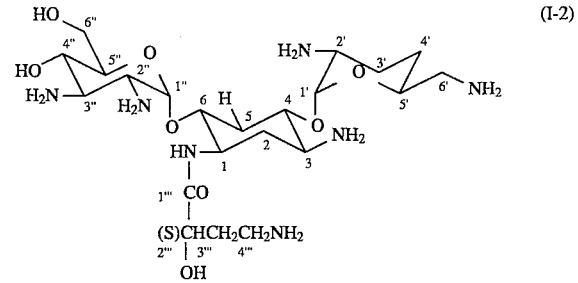

or a pharmaceutically acceptable acid addition salt thereof.

2. 2"-Amino-5,2"-dideoxydibekacin having the formula

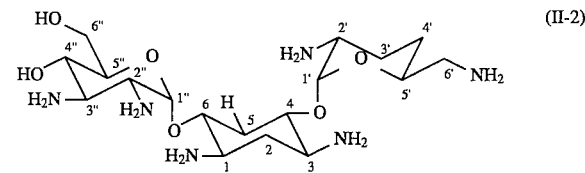

or a pharmaceutically acceptable acid addition salt thereof.

3. 2"-Amino-5,2"-dideoxy-5-epi-aminoarbekacin having the formula

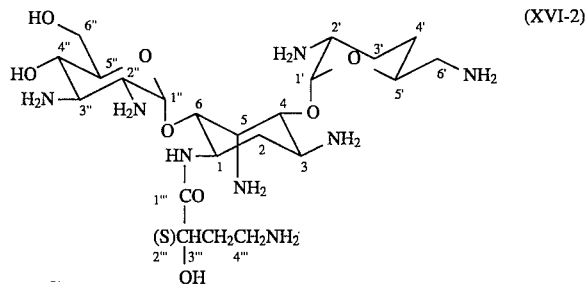

or a pharmaceutically acceptable acid addition salt thereof.

4. An antibacterial composition comprising an antibacterially effective amount of 2"-amino-5,2"-dideoxyarbekacin according to claim 1 or a pharmaceutically acceptable acid addition salt thereof as active ingredient, in combination with a pharmaceutically acceptable carrier for the active ingredient.

5. An antibacterial composition comprising an antibacterially effective amount of 2"-amino-5,2"-dideoxydibekacin according to claim 2 or a pharmaceutically acceptable acid addition salt thereof as active ingredient, in combination with a pharmaceutically acceptable carrier for the active ingredient.

6. An antibacterial composition comprising an antibacterially effective amount of 2"-amino-5,2"-dideoxy-5-epi-aminoarbekacin according to claim 3 or a pharmaceutically acceptable acid addition salt thereof as active ingredient, in combination with a pharmaceutically acceptable carrier for the active ingredient.

* * * * *